(12) United States Patent
Osakabe et al.

(10) Patent No.: US 12,406,752 B2
(45) Date of Patent: Sep. 2, 2025

(54) SYSTEM FOR GENERATING COMPOUND STRUCTURE REPRESENTATION

(71) Applicant: Hitachi, Ltd., Tokyo (JP)

(72) Inventors: Yoshihiro Osakabe, Tokyo (JP); Akinori Asahara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 403 days.

(21) Appl. No.: 17/919,804

(22) PCT Filed: Apr. 9, 2021

(86) PCT No.: PCT/JP2021/015042
§ 371 (c)(1),
(2) Date: Oct. 19, 2022

(87) PCT Pub. No.: WO2021/220774
PCT Pub. Date: Nov. 4, 2021

(65) Prior Publication Data
US 2023/0117325 A1    Apr. 20, 2023

(30) Foreign Application Priority Data
Apr. 28, 2020 (JP) ................................. 2020-079790

(51) Int. Cl.
*G16C 20/90* (2019.01)
*G16C 20/70* (2019.01)
*G16C 20/80* (2019.01)

(52) U.S. Cl.
CPC ............ *G16C 20/90* (2019.02); *G16C 20/70* (2019.02); *G16C 20/80* (2019.02)

(58) Field of Classification Search
CPC ........ G16C 20/90; G16C 20/70; G16C 20/80; G16C 20/50; G16C 20/30; G06N 3/0455; G06N 3/047; G06N 3/088
See application file for complete search history.

(56) References Cited

U.S. PATENT DOCUMENTS 5,566,083 A * 10/1996 Fang ...................... G01R 31/30
703/4
7,487,078 B1 * 2/2009 Phillips .................. G06F 30/367
703/19
(Continued)

OTHER PUBLICATIONS

Extended European Search Report received in corresponding European Application No. 21796144.0 dated May 10, 2024.
(Continued)

*Primary Examiner* — Tung S Lau
(74) *Attorney, Agent, or Firm* — MATTINGLY & MALUR, PC

(57) ABSTRACT

A structure model includes a first encoder that converts a compound structure representation to a real number vector and a first decoder that estimates the compound structure representation from the real number vector resulting from the conversion by the first encoder. A structure-property relationship model includes a second encoder that converts, to a real number vector, an extended vector including, as components, the real number vector generated by the first encoder and a target value vector including target values of one or more physical property values and a second decoder that estimates the extended vector from the real number vector generated by the second encoder.

8 Claims, 21 Drawing Sheets

(56) References Cited

U.S. PATENT DOCUMENTS

| | | | | |
|---|---|---|---|---|
| 8,706,427 | B2* | 4/2014 | Haque | G16C 20/40 |
| | | | | 702/32 |
| 8,886,497 | B1* | 11/2014 | Vold | G06F 17/13 |
| | | | | 703/2 |
| 2009/0204375 | A1* | 8/2009 | Hirose | G06F 30/20 |
| | | | | 977/839 |
| 2014/0257527 | A1* | 9/2014 | Chinesta | G05B 13/04 |
| | | | | 700/29 |
| 2018/0180561 | A1* | 6/2018 | Makhotkin | G01N 23/20 |
| 2018/0239853 | A1* | 8/2018 | Shimizu | G06F 30/23 |

OTHER PUBLICATIONS

Blaschke, Thomas et al, "Application of Generative Autoencoder in De Novo Molecular Design", Molecular Informatics, Dec. 13, 2017, pp. 1-11, vol. 37, Hoboken USA.

Bjerrum, Jannik, "Improving Chemical Autoencoder Latent Space and Molecular De novo Generation Diversity with Heteroencoders", Biomolecules, Oct. 30, 2018, pp. 1-17, vol. 8, No. 4.

Osakabe, Yoshihiro et al., "MatVAE: Independently Trained Nested Variational Autoencoder for Generating Chemical Structural Formula", Mar. 2021, AAAI 2021 Spring Symposium on Combining Artificial Intelligence and Machine Learning with Physics Sciences, Stanford, CA.

Rafael Gomez-Bombarelli et al., "Automatic Chemical Design Using a Data-Driven Continuous Representation of Molecules" ACS Central Science, vol. 4, No. 2, pp. 268-2766, Feb. 2018.

Diederik P. Kingma et al., "Semi-supervised Learning with Deep Generative Models", NIPS 2014.

International Search Report of PCT/JP2021/015042 dated Jul. 6, 2021.

* cited by examiner

FIG. 3

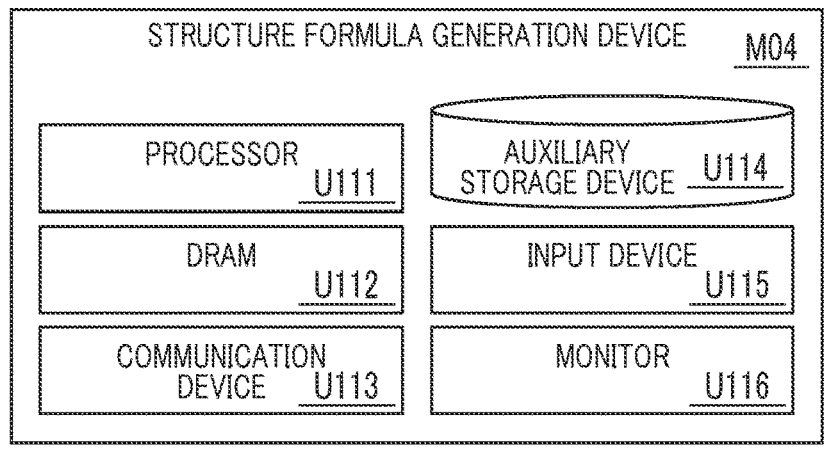

STRUCTURE FORMULA GENERATION DEVICE M04

- PROCESSOR U111
- DRAM U112
- COMMUNICATION DEVICE U113
- AUXILIARY STORAGE DEVICE U114
- INPUT DEVICE U115
- MONITOR U116

FIG. 4

CATALOG DATA  DB10

| Table ID T0C1 | Table Type T0C2 | ID T0C3 | SMILES T0C4 |
|---|---|---|---|
| Tbl_Cat_001 | Catalog | ZINC000000001084 | Cn1cnc2c1c(=O)n(C)c(=O)n2C |
| Tbl_Cat_001 | Catalog | ZINC000000001447 | Cn1c2nncnc2c(=O)n(C)c1=O |
| Tbl_Cat_001 | Catalog | ZINC000000002151 | Cn1cnc2c1c(=O)[nH]c(=O)n2C |
| Tbl_Cat_001 | Catalog | ZINC000000008657 | NC(=O)c1ncc[nH]c1=O |
| Tbl_Cat_001 | Catalog | ZINC00000049143 | Cc1[nH]c(=O)[nH]c(=O)c1CO |
| ⋮ | ⋮ | ⋮ | ⋮ |

FIG. 5

EXPERIMENT DATA  DB11

| Table ID T1C1 | Table Type T1C2 | ID T1C3 | SMILES T1C4 | MWt T1C5 | logP T1C6 |
|---|---|---|---|---|---|
| Tbl_Exp_001 | Experiment | ZINC000001532558 | O=C(O)C(=O)CO | 104.061 | −1.368 |
| Tbl_Exp_001 | Experiment | ZINC000001532759 | O=C(O)C(=O)C(=O)O | 118.044 | −1.275 |
| Tbl_Exp_001 | Experiment | ZINC000001534133 | O=C(O)CNC(=O)C(=O)O | 147.086 | −1.728 |
| Tbl_Exp_001 | Experiment | ZINC000001555345 | CNCC(N)=O | 88.110 | −1.309 |
| Tbl_Exp_001 | Experiment | ZINC000001556606 | NC(=O)N1CCNCC1 | 129.163 | −1.030 |
| ⋮ | ⋮ | ⋮ | ⋮ | ⋮ | ⋮ |

FIG. 6

STRUCTURE FORMULA MATRIX DATABASE — DB14

CATALOG-DATA-STRUCTURE-FORMULA MATRIX TABLE — 141

| Table ID<br>T3C1 | Table Type<br>T3C2 | ID<br>T3C3 | SMILES<br>T3C4 | STRUCTURE FORMULA MATRIX<br>T3C5 |
|---|---|---|---|---|
| Tbl_Cat_001 | Catalog | ZINC000000001084 | Cn1cnc2c1c(=O)n(C)c(=O)n2C | [ [1, 0, 0,...],<br>[0, 1, 0,...],<br>[0, 0, 0,...],<br>... ] |
| Tbl_Cat_001 | Catalog | ZINC000000001447 | Cn1c2nncnc2c(=O)n(C)c1=O | [ [1, 0, 0,...],<br>[0, 1, 0,...],<br>[0, 0, 0,...],<br>... ] |
| Tbl_Cat_001 | Catalog | ZINC000000002151 | Cn1cnc2c1c(=O)[nH]c(=O)n2C | [ [1, 0, 0,...],<br>[0, 1, 0,...],<br>[0, 0, 0,...],<br>... ] |
| Tbl_Cat_001 | Catalog | ZINC000000008657 | NC(=O)c1ncc[nH]c1=O | [ [0, 0, 1,...],<br>[0, 0, 0,...],<br>[0, 0, 0,...],<br>... ] |
| ⋮ | ⋮ | ⋮ | ⋮ | ⋮ |

EXPERIMENT-DATA-STRUCTURE-FORMULA MATRIX TABLE — 142

| Table ID<br>T4C1 | Table Type<br>T4C2 | ID<br>T4C3 | SMILES<br>T4C4 | MWt<br>T4C5 | logP<br>T4C6 | STRUCTURE FORMULA MATRIX<br>T4C7 |
|---|---|---|---|---|---|---|
| Tbl_Exp_001 | Experiment | ZINC000001532558 | O=C(O)C(=O)CO | 104.061 | −1.368 | [ [0, 0, 0,...],<br>[0, 0, 0,...],<br>[0, 0, 0,...],<br>... ] |
| Tbl_Exp_001 | Experiment | ZINC000001532759 | O=C(O)C(=O)C(=O)O | 118.044 | −1.275 | [ [0, 0, 0,...],<br>[0, 0, 0,...],<br>[0, 0, 0,...],<br>... ] |
| Tbl_Exp_001 | Experiment | ZINC000001534133 | O=C(O)CNC(=O)C(=O)O | 147.086 | −1.728 | [ [0, 0, 0,...],<br>[0, 0, 0,...],<br>[0, 0, 0,...],<br>... ] |
| Tbl_Exp_001 | Experiment | ZINC000001555345 | CNCC(N)=O | 88.110 | −1.309 | [ [0, 0, 0,...],<br>[0, 0, 0,...],<br>[0, 0, 0,...],<br>... ] |
| ⋮ | ⋮ | ⋮ | ⋮ | ⋮ | ⋮ | ⋮ |

FIG. 7

TRAINING DATABASE DB15

STRUCTURE MODEL TABLE ~151

| Table ID<br>T5C1 | Table Type<br>T5C2 | ID<br>T5C3 | SMILES<br>T5C4 | STRUCTURE FORMULA MATRIX<br>T5C5 |
|---|---|---|---|---|
| Tbl_G_100 | Catalog | ZINC000000001084 | Cn1cnc2c1c(=O)n(C)c(=O)n2C | [ [1, 0, 0,...],<br>[0, 1, 0,...],<br>[0, 0, 0,...],<br>... ] |
| Tbl_G_100 | Catalog | ZINC000000001447 | Cn1c2nncnc2c(=O)n(C)c1=O | [ [1, 0, 0,...],<br>[0, 1, 0,...],<br>[0, 0, 0,...],<br>... ] |
| Tbl_G_100 | Catalog | ZINC000000002151 | Cn1cnc2c1c(=O)[nH]c(=O)n2C | [ [1, 0, 0,...],<br>[0, 1, 0,...],<br>[0, 0, 0,...],<br>... ] |
| Tbl_G_100 | Catalog | ZINC000000008657 | NC(=O)c1ncc[nH]c1=O | [ [0, 0, 1,...],<br>[0, 0, 0,...],<br>[0, 0, 0,...],<br>... ] |
| ⋮ | ⋮ | ⋮ | ⋮ | ⋮ |

STRUCTURE-PROPERTY RELATIONSHIP MODEL TABLE ~152

| Table ID<br>T6C1 | Table Type<br>T6C2 | ID<br>T6C3 | SMILES<br>T6C4 | MWt<br>T6C5 | logP<br>T6C6 | STRUCTURE FORMULA MATRIX<br>T6C7 |
|---|---|---|---|---|---|---|
| Tbl_R_100 | Experiment | ZINC000001532558 | O=C(O)C(=O)CO | 104.061 | -1.368 | [ [0, 0, 0,...],<br>[0, 0, 0,...],<br>[0, 0, 0,...],<br>... ] |
| Tbl_R_100 | Experiment | ZINC000001532759 | O=C(O)C(=O)C(=O)O | 118.044 | -1.275 | [ [0, 0, 0,...],<br>[0, 0, 0,...],<br>[0, 0, 0,...],<br>... ] |
| Tbl_R_100 | Experiment | ZINC000001534133 | O=C(O)CNC(=O)C(=O)O | 147.086 | -1.728 | [ [0, 0, 0,...],<br>[0, 0, 0,...],<br>[0, 0, 0,...],<br>... ] |
| Tbl_R_100 | Experiment | ZINC000001555345 | CNCC(N)=O | 88.110 | -1.309 | [ [0, 0, 0,...],<br>[0, 0, 0,...],<br>[0, 0, 0,...],<br>... ] |
| ⋮ | ⋮ | ⋮ | ⋮ | ⋮ | ⋮ | ⋮ |

```
INITIAL PARAMETER    DB13

{
  "CatalogData Tables": ["Tbl_Cat_001"],
  "ExperimentData Tables": ["Tbl_Exp_001"],
  "Target Properties": ["MWt", "logP"],
  "Target Property Values": {"MWt": 1.249, "logP": -1.121},
  "Number_of_vae_relation": 1,
  "VAE_Initial_Params":[
                              "vae_grammar_layers":
                                 [["enc": [...],
                                   "dec": [...]]
                                 ],
                              "vae_relation_layers":
                                 [["enc": [...],
                                   "dec": [...]]
                                 ],
                              "middle_dims": [9,7],
                              ......
                        ],
  ......
}
```

NETWORK STRUCTURE
CONFIRMATION SCREEN

MODEL TABLE

| Network ID T7C1 | Network Order T7C2 | Nest Order T7C3 | Target T7C4 |
|---|---|---|---|
| #enc_01 | 1 | 1 | {"Tbl_G_100": ["STRUCTURE FORMULA MATRIX"]} |
| #enc_02 | 2 | 2 | {"Tbl_R_100": ["MWt","logP"]} |
| #dec_02 | 3 | 2 | {"Tbl_R_100": ["MWt","logP"]} |
| #dec_01 | 4 | 1 | {"Tbl_G_100": ["STRUCTURE FORMULA MATRIX"]} |

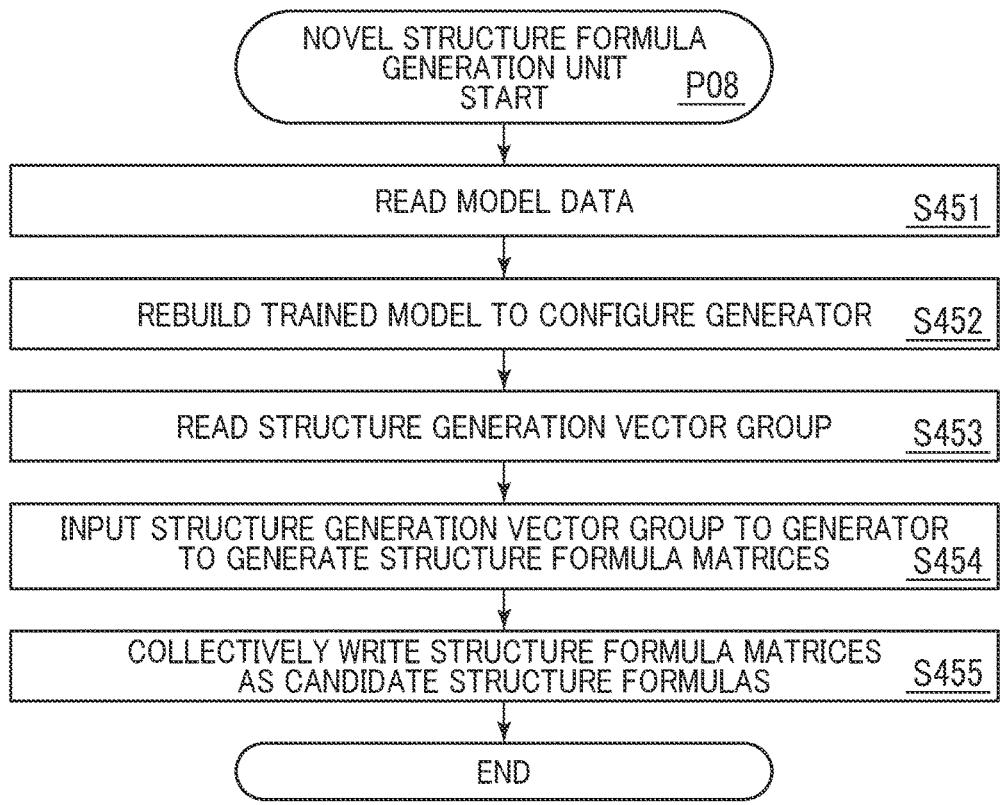
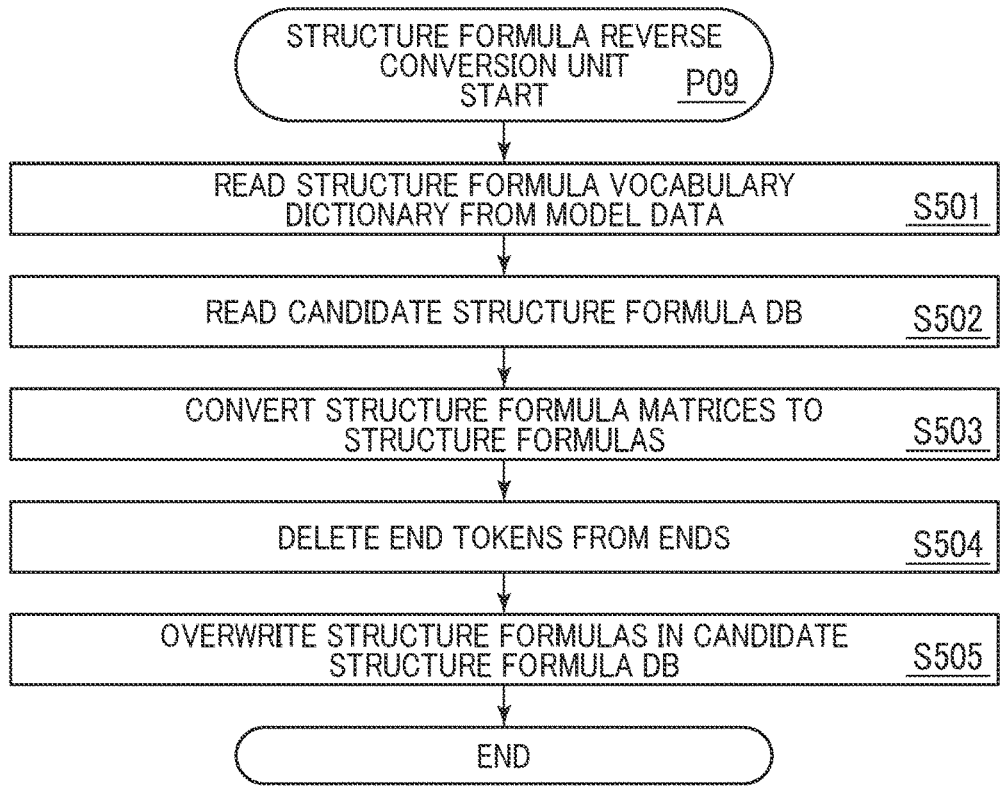

FIG. 22

TRAINING DATABASE DB15

TRAINING TABLE FOR FIRST VAE IN STRUCTURE-PROPERTY RELATIONSHIP MODEL — 153

| Table ID<br>T8C1 | Table Type<br>T8C2 | ID<br>T8C3 | SMILES<br>T8C4 | MWt<br>T8C5 | STRUCTURE FORMULA MATRIX<br>T8C7 |
|---|---|---|---|---|---|
| Tbl_R_201 | Experiment | ZINC000001532558 | O=C(O)C(=O)CO | 104.061 | [[0, 0, 0,...],<br>[0, 0, 0,...],<br>[0, 0, 0,...],<br>...] |
| Tbl_R_201 | Experiment | ZINC000001532759 | O=C(O)C(=O)C(=O)O | 118.044 | [[0, 0, 0,...],<br>[0, 0, 0,...],<br>[0, 0, 0,...],<br>...] |
| Tbl_R_201 | Experiment | ZINC000001534133 | O=C(O)CNC(=O)C(=O)O | 147.086 | [[0, 0, 0,...],<br>[0, 0, 0,...],<br>[0, 0, 0,...],<br>...] |
| Tbl_R_201 | Experiment | ZINC000001555345 | CNCC(N)=O | 88.110 | [[0, 0, 0,...],<br>[0, 0, 0,...],<br>[0, 0, 0,...],<br>...] |
| ⋮ | ⋮ | ⋮ | ⋮ | ⋮ | ⋮ |

TRAINING TABLE FOR SECOND VAE IN STRUCTURE-PROPERTY RELATIONSHIP MODEL — 154

| Table ID<br>T9C1 | Table Type<br>T9C2 | ID<br>T9C3 | SMILES<br>T9C4 | MWt<br>T9C5 | logP<br>T9C6 | STRUCTURE FORMULA MATRIX<br>T9C7 |
|---|---|---|---|---|---|---|
| Tbl_R_202 | Experiment | ZINC000001532558 | O=C(O)C(=O)CO | 104.061 | -1.368 | [[0, 0, 0,...],<br>[0, 0, 0,...],<br>[0, 0, 0,...],<br>...] |
| Tbl_R_202 | Experiment | ZINC000001532759 | O=C(O)C(=O)C(=O)O | 118.044 | -1.275 | [[0, 0, 0,...],<br>[0, 0, 0,...],<br>[0, 0, 0,...],<br>...] |
| Tbl_R_202 | Experiment | ZINC000001534133 | O=C(O)CNC(=O)C(=O)O | 147.086 | -1.728 | [[0, 0, 0,...],<br>[0, 0, 0,...],<br>[0, 0, 0,...],<br>...] |
| Tbl_R_202 | Experiment | ZINC000001555345 | CNCC(N)=O | 88.110 | -1.309 | [[0, 0, 0,...],<br>[0, 0, 0,...],<br>[0, 0, 0,...],<br>...] |
| ⋮ | ⋮ | ⋮ | ⋮ | ⋮ | ⋮ | ⋮ |

MODEL TABLE 172

| Network ID T10C1 | Network Order T10C2 | Nest Order T10C3 | Target T10C4 |
|---|---|---|---|
| #enc_01 | 1 | 1 | ["Tbl_G_100": ["STRUCTURE FORMULA MATRIX"]] |
| #enc_02 | 2 | 2 | ["Tbl_R_201": ["MWt"]] |
| #enc_03 | 3 | 3 | ["Tbl_R_202": ["logP"]] |
| #dec_03 | 4 | 3 | ["Tbl_R_202": ["logP"]] |
| #dec_02 | 5 | 2 | ["Tbl_R_201": ["MWt"]] |
| #dec_01 | 6 | 1 | ["Tbl_G_100": ["STRUCTURE FORMULA MATRIX"]] |

NETWORK STRUCTURE CONFIRMATION SCREEN

FIG. 25

TRAINING DATABASE    DB15

TRAINING TABLE FOR FIRST VAE IN STRUCTURE-PROPERTY RELATIONSHIP MODEL ~155

| Table ID<br>T11C1 | Table Type<br>T11C2 | ID<br>T11C3 | SMILES<br>T11C4 | Prop1<br>T11C5 | STRUCTURE FORMULA MATRIX<br>T11C7 |
|---|---|---|---|---|---|
| Tbl_R_301 | Experiment | ZINC000001532558 | O=C(O)C(=O)CO | 104.061 | [...] |
| Tbl_R_301 | Experiment | ZINC000001532759 | O=C(O)C(=O)C(=O)O | 118.044 | [...] |
| ⋮ | ⋮ | ⋮ | ⋮ | ⋮ | ⋮ |

TRAINING TABLE FOR SECOND VAE IN STRUCTURE-PROPERTY RELATIONSHIP MODEL ~156

| Table ID<br>T12C1 | Table Type<br>T12C2 | ID<br>T12C3 | SMILES<br>T12C4 | Prop1<br>T12C5 | Prop2<br>T12C6 | Prop3<br>T12C7 | STRUCTURE FORMULA MATRIX<br>T12C8 |
|---|---|---|---|---|---|---|---|
| Tbl_R_302 | Experiment | ZINC000001532558 | O=C(O)C(=O)CO | 104.061 | -1.368 | 5.124 | [...] |
| Tbl_R_302 | Experiment | ZINC000001532759 | O=C(O)C(=O)C(=O)O | 118.044 | -1.275 | 5.388 | [...] |
| ⋮ | ⋮ | ⋮ | ⋮ | ⋮ | ⋮ | ⋮ | ⋮ |

FIG. 26

MODEL TABLE ~173

| Network ID<br>T13C1 | Network Order<br>T13C2 | Nest Order<br>T13C3 | Target<br>T13C4 |
|---|---|---|---|
| #enc_01 | 1 | 1 | {"Tbl_G_100": ["STRUCTURE FORMULA MATRIX"]} |
| #enc_02 | 2 | 2 | {"Tbl_R_301": ["Prop1"]} |
| #enc_03 | 3 | 3 | {"Tbl_R_302": ["Prop2","Prop3"]} |
| #dec_03 | 4 | 3 | {"Tbl_R_302": ["Prop2","Prop3"]} |
| #dec_02 | 5 | 2 | {"Tbl_R_301": ["Prop1"]} |
| #dec_01 | 6 | 1 | {"Tbl_G_100": ["STRUCTURE FORMULA MATRIX"]} |

STRUCTURE-PROPERTY RELATIONSHIP MODEL TRAINING DATA

| CHEMICAL STRUCTURE FORMULA | PHYSICAL PROPERTY VALUE (Prop1) | PHYSICAL PROPERTY VALUE (Prop2) |
|---|---|---|
| ... | ... | ... |
| ... | ... | ... |
| ... | ... | ... |
| ... | ... | ✗ |
| ... | ... | ✗ |
| ... | ... | ✗ |

312 = top three rows
311 = bottom three rows

NETWORK STRUCTURE CONFIRMATION SCREEN

MODEL TABLE 174

| Network ID<br>T14C1 | Network Order<br>T14C2 | Nest Order<br>T14C3 | Target<br>T14C4 |
|---|---|---|---|
| #enc_01 | 1 | 1 | ["Tbl_G_100": ["STRUCTURE FORMULA MATRIX"]] |
| #enc_02 | 2 | 2 | ["Tbl_R_401": ["Prop1"]] |
| #enc_03 | 3 | 3 | ["Tbl_R_402": ["Prop2"]] |
| #dec_03 | 4 | 3 | ["Tbl_R_402": ["Prop2"]] |
| #dec_02 | 5 | 2 | ["Tbl_R_401": ["Prop1"]] |
| #dec_01 | 6 | 1 | ["Tbl_G_100": ["STRUCTURE FORMULA MATRIX"]] |

FIG. 31

| Table ID | Table Type | ID | SMILES | Prop1 | Prop2 | STRUCTURE FORMULA MATRIX |
|---|---|---|---|---|---|---|
| T15C1 | T15C2 | T15C3 | T15C4 | T15C5 | T15C6 | T15C7 |
| Tbl_Exp_011 | Experiment | ZINC000001532558 | O=C(O)C(=O)CO | 104.061 | -1.368 | [...] |
| Tbl_Exp_011 | Experiment | ZINC000001532759 | O=C(O)C(=O)C(=O)O | 118.044 | -1.275 | [...] |
| Tbl_Exp_013 | Experiment | ZINC000001532449 | O=C(O)CCCC(=O)O | 123.044 | -2.133 | [...] |
| ⋮ | ⋮ | ⋮ | ⋮ | ⋮ | ⋮ | ⋮ |
| Tbl_Exp_012 | Experiment | ZINC000001534133 | O=C(O)CNC(=O)C(=O)O | 147.086 | Null | [...] |
| Tbl_Exp_012 | Experiment | ZINC000001555345 | CNCC(N)=O | 88.110 | Null | [...] |
| Tbl_Exp_012 | Experiment | ZINC000001556606 | NC(=O)N1CCNCC1 | 129.163 | Null | [...] |
| Tbl_Exp_013 | Experiment | ZINC000001532451 | O=C(OOC)CC(=OC)O | 149.044 | Null | [...] |
| ⋮ | ⋮ | ⋮ | ⋮ | ⋮ | ⋮ | ⋮ |

150

TRAINING TABLE FOR FIRST VAE IN STRUCTURE-PROPERTY RELATIONSHIP MODEL

| Table ID | Table Type | ID | SMILES | Prop1 | STRUCTURE FORMULA MATRIX |
|---|---|---|---|---|---|
| T16C1 | T16C2 | T16C3 | T16C4 | T16C5 | T16C7 |
| Tbl_R_401 | Experiment | ZINC000001532558 | O=C(O)C(=O)CO | 104.061 | [...] |
| Tbl_R_401 | Experiment | ZINC000001532759 | O=C(O)C(=O)C(=O)O | 118.044 | [...] |
| Tbl_R_401 | Experiment | ZINC000001532449 | O=C(O)CCCC(=O)O | 123.044 | [...] |
| ⋮ | ⋮ | ⋮ | ⋮ | ⋮ | ⋮ |
| Tbl_R_401 | Experiment | ZINC000001534133 | O=C(O)CNC(=O)C(=O)O | 147.086 | [...] |
| Tbl_R_401 | Experiment | ZINC000001555345 | CNCC(N)=O | 88.110 | [...] |
| Tbl_R_401 | Experiment | ZINC000001556606 | NC(=O)N1CCNCC1 | 129.163 | [...] |
| Tbl_R_401 | Experiment | ZINC000001532451 | O=C(OOC)CC(=OC)O | 149.044 | [...] |
| ⋮ | ⋮ | ⋮ | ⋮ | ⋮ | ⋮ |

157

TRAINING TABLE FOR SECOND VAE IN STRUCTURE-PROPERTY RELATIONSHIP MODEL

| Table ID | Table Type | ID | SMILES | Prop1 | Prop2 | STRUCTURE FORMULA MATRIX |
|---|---|---|---|---|---|---|
| T17C1 | T17C2 | T17C3 | T17C4 | T17C5 | T17C6 | T17C7 |
| Tbl_R_402 | Experiment | ZINC000001532558 | O=C(O)C(=O)CO | 104.061 | -1.368 | [...] |
| Tbl_R_402 | Experiment | ZINC000001532759 | O=C(O)C(=O)C(=O)O | 118.044 | -1.275 | [...] |
| Tbl_R_402 | Experiment | ZINC000001532449 | O=C(O)CCCC(=O)O | 123.044 | -2.133 | [...] |
| ⋮ | ⋮ | ⋮ | ⋮ | ⋮ | ⋮ | ⋮ |

158

SYSTEM FOR GENERATING COMPOUND STRUCTURE REPRESENTATION

CLAIM OF PRIORITY

The present application claims priority from Japanese Patent Application JP2020-079790 filed on Apr. 28, 2020, the content of which is hereby incorporated by reference into this application.

TECHNICAL FIELD

The present invention relates to a system for generating candidates for a compound structure representation expected to have a desired physical property value.

BACKGROUND ART

For a novel material search task, a virtual screening method is used. An example of the virtual screening method is disclosed in, e.g., Nonpatent Literature 1. In virtual screening, a machine learning model is applied to data on a known compound to configure a physical property estimation model to which a chemical structure formula represented in a predetermined representational form is input. Then, to randomly generated chemical structure formulas, the physical property estimation model mentioned above is applied. Screening is performed on the basis of prediction values thus calculated, and the chemical structure formula expected to have a physical property value exceeding a threshold is presented as a candidate.

Nonpatent Literature 2 as another prior art literature discloses stacked semi-supervised learning models that execute an image classification task. Nonpatent Literature 2 discloses that training of the outer models among the stacked models is performed using unlabeled training data, while training of the inner models is performed using labeled training data.

CITATION LIST

Nonpatent Literatures

Nonpatent Literature 1: R. Gomez-Bombarelli et al., "Automatic Chemical Design Using a Data-Driven Continuous Representation of Molecules," ACS Cent. Sci., vol. 4, no. 2, pp. 268-276, February 2018.

Nonpatent Literature 2: D. P. Kingma, D. J. Rezende, S. Mohamed, and M. Welling, "Semi-supervised Learning with Deep Generative Models," NIPS 2014.

SUMMARY OF INVENTION

Technical Problem

A conventional search method using a physical property value estimation model is an interpolative search method which allows estimation to be performed only in a range of training data, and is therefore inappropriate for an extrapolative search intended to find a novel material having a physical property value exceeding performance of known materials.

In the conventional virtual screening method, a relationship between a representation form of a chemical structure formula, such as SMILES (Simplified Molecular Input Line Entry System), and a physical property value is acquired using a model such as a neural network. Thus, it is intended to generate a chemical structure formula having a desired physical property value. However, to acquire both of grammar rules for the representation form of the chemical structure formula and a relationship between the chemical structure formula and the physical property value by learning, a large amount of data including sets of chemical structure formulas and physical property values is required. However, it is difficult to prepare a large amount of data including sets of chemical structure formulas and physical property values, such as experiment data or a simulation result.

Therefore, a technique capable of generating a learning model that can present candidates for a compound having physical property values superior to physical property values included in training data by using data including a smaller number of sets of chemical structure formulas and physical property values is desired.

Solution to Problem (I) An aspect of the present invention is a system for generating a compound structure representation, the system including: one or more processors; and one or more storage devices. Each of the one or more storage devices stores a structure model, a structure-property relationship model, a compound structure representation of each of one or more known materials, and one or more target values of each of one or more types of physical property values. The structure model includes: a first encoder that converts the compound structure representation to a real number vector; and a first decoder that estimates the compound structure representation from the real number vector resulting from the conversion by the first encoder. The structure-property relationship model includes: a second encoder that converts, to a real number vector, an input vector including, as components, the real number vector generated by the first encoder and a target value vector including the target values of the one or more types of physical property values; and a second decoder that estimates the input vector from the real number vector generated by the second encoder. Each of the one or more processors generates, using the first encoder of the structure model, one or more structure generation vectors on the basis of each of the compound structure representation of each of the one or more known materials and the one or more target values of each of the one or more types of physical property values. Each of the one or more structure generation vectors includes, as components, the real number vector of the compound structure representation of one of the known materials generated by the first encoder and the target value vector including the target values of each of the one or more types of physical property values. Each of the one or more processors inputs, to the structure-property relationship model, each of the one or more structure generation vectors. Each of the one or more processors extracts, from an output of the second decoder of the structure-property relationship model, the real number vector corresponding to the compound structure representation. Each of the one or more processors inputs the extracted real number vector to the first decoder of the structure model to generate a novel compound structure representation.

Advantageous Effects of Invention

According to the aspect of the present invention, it is possible to generate a learning model that can present candidates for a compound having physical property values superior to physical property values included in training data by using data including a smaller number of sets of chemical structure formulas and physical property values.

BRIEF DESCRIPTION OF DRAWINGS

FIG. 3 illustrates an example of a hardware configuration of a structure formula generation device;

FIG. 4 illustrates an example of a configuration of catalog data;

FIG. 5 illustrates an example of a configuration of experiment data;

FIG. 6 illustrates an example of data included in a structure formula matrix database;

FIG. 7 illustrates an example of data included in a training database;

FIG. 18 illustrates a flow chart of an example of processing by a novel structure formula generation unit;

FIG. 19 illustrates a flow chart of an example of processing by a structure formula reverse conversion unit;

FIG. 22 illustrates an example of data included in the training database according to the second embodiment;

FIG. 25 illustrates an example of data included in a training database DB according to the third embodiment;

FIG. 26 illustrates an example of a configuration of a model table included in a model data DB according to the third embodiment;

FIG. 31 illustrates an example in which the training data generation unit generates the structure-property relationship model training data from the experiment data.

DESCRIPTION OF EMBODIMENTS

In the following, if necessary for the sake of convenience, each of the embodiments will be described by being divided into a plurality of sections or embodiments. However, they are by no means irrelevant to each other unless particularly explicitly described otherwise, but are in relations such that one of the sections or embodiments is modifications, details, supplementary explanation, and so forth of part or the whole of the others. Also, in the following, when the number and the like (including the number, numerical value, amount, range, and the like) of elements are mentioned, they are not limited to the specified numbers unless particularly explicitly described otherwise or unless they are obviously limited to specified numbers in principle. The number and the like of the elements may be not less than or not more than the specified numbers.

The present system may be a physical computer system (one or more physical computers), or may also be a system built on a computing resource group (a plurality of computing resources) such as a cloud infrastructure. The computer system or the computing resource group includes one or more interface devices (including, e.g., a communication device and an input/output device), one or more storage devices (including, e.g., a memory (main storage) and an auxiliary storage device), and one or more processors.

When a function is implemented through execution of a program by the processor, determined processing is performed, while the storage device and/or the interface device or the like are used appropriately, and therefore the function may also be assumed to be at least a part of the processor. Processing described by using the function as a subject may also be assumed to be processing to be performed by the processor or the system including the processor. The program may also be installed from a program source. The program source may be, e.g., a program distributed computer or a computer readable storage medium (e.g., a computer-readable non-transitory storage medium). A description of each function is given as an example, and a plurality of functions may be integrated into one function or one function may be divided into a plurality of functions.

[Outline]

The following will disclose a technology of estimating a chemical structure formula expected to have desired physical property values. The chemical structure formula may be represented in various representational forms. An example of the representational forms for the chemical structure formula may be a character string written according to given grammar rules or a matrix. Examples of the grammar rules include SMILES (Simplified Molecular Input Line Entry System). Each of embodiments described below uses SMILES as an example of the grammar rules for describing the chemical structure formula.

Figure 1:
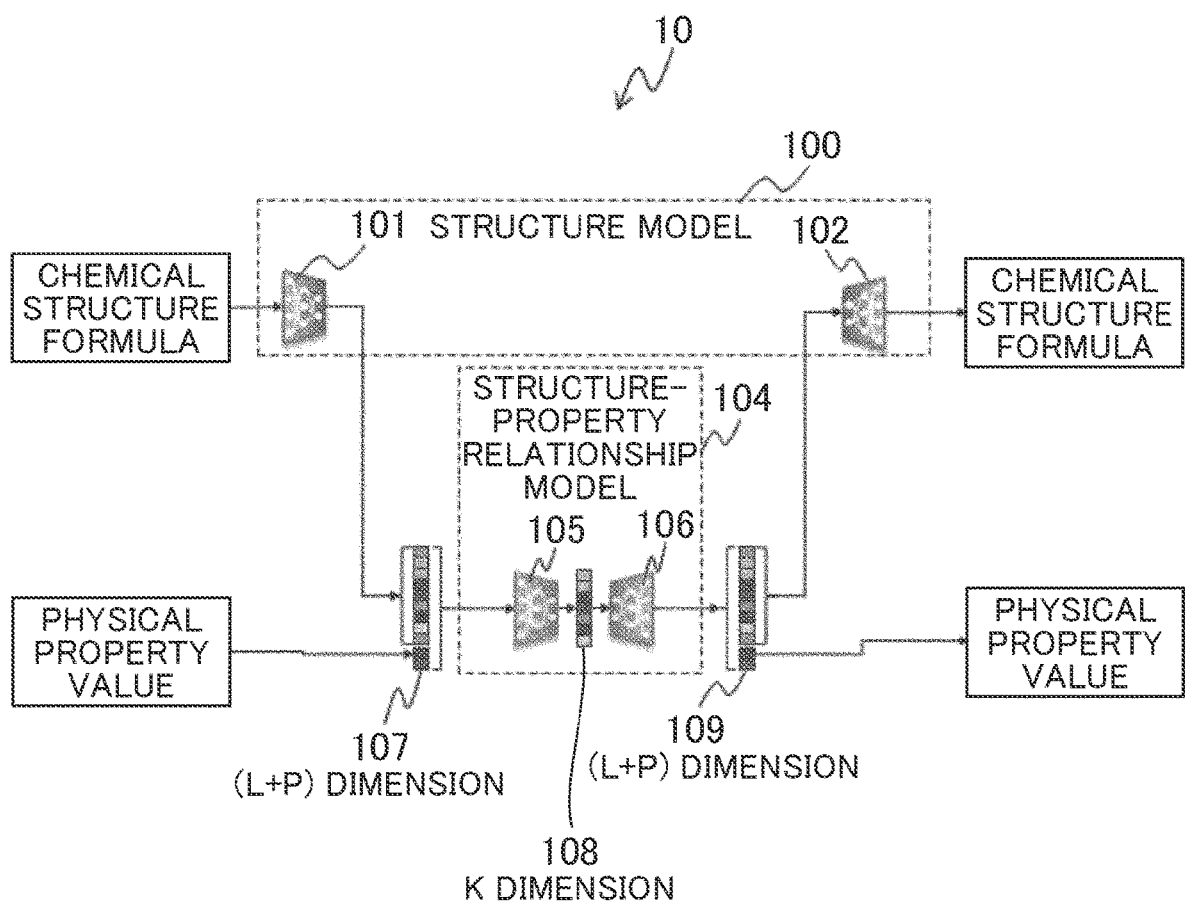
FIG. 1 schematically illustrates an example of a configuration of a chemical structure formula generation model according to each of embodiments of the present description.

FIG. 1 schematically illustrates an example of a configuration of a chemical structure formula generation model according to each of the embodiments of the present description. A chemical structure formula generation model 10 receives, as inputs, a representation representing a known chemical structure formula and target physical property values, and outputs a representation of a novel chemical structure formula expected to have physical property values close to the target physical property values.

The chemical structure formula generation model 10 is a combination of two types of models which are a structure model 100 intended to learn a chemical structure formula and a structure-property relationship model 104 that learns relationships between feature values of the chemical structure formula and physical property values thereof. The structure model 100 includes one variational auto-encoder (VAE), while the structure-property relationship model 104 includes one or more VAEs. In the example of the configuration in FIG. 1, the structure-property relationship model 104 includes the single VAE.

The VAE is a type of auto-encoder, which is a deep generation model including two neural networks, which are an encoder and a decoder. The encoder converts an input (a vector) to a real number vector. A space to which the real number vector belongs is referred to as a latent space, and is assumed to follow a given distribution, e.g., a normal distribution. The decoder reversely converts the real number vector to output a vector in a dimension equal to that of the input.

Each of the encoder and decoder is trained (learn) to have the input and the output equal to each other. The ability to reconfigure the input from the real number vector corresponding to an intermediate output means that sufficient features of the input are reflected in the real number vector. A dimension of the latent space is set to be lower than a dimension of the input. Accordingly, the encoder can extract feature values of the input and also compress the dimension of the input.

The vector corresponding to the intermediate output is referred to as a latent variable or a latent representation, which is an abstract representation representing features extracted from a structure formula matrix representing the chemical structure formula. The structure formula matrix can be obtained by converting, e.g., a character string representing a chemical structure formula of a material. The latent variable is assumed to follow a given distribution, e.g., a Gaussian distribution. Accordingly, when receiving a vector with added noise, the decoder can restore the input structure formula matrix with high accuracy. Thus, the VAE serving as the generation model has high robustness.

As illustrated in FIG. 1, the chemical structure formula generation model 10 has a nesting structure. Specifically, between an encoder 101 and a decoder 102 of the structure model (outer VAE) 100, the structure-property relationship model 104 is disposed. In the example in FIG. 1, the structure-property relationship model 104 includes an encoder 105 and a decoder 106. As will be described later, the structure-property relationship model 104 can include a plurality of the VAEs (inner VAEs), and each of the inner VAEs is disposed between the encoder and the decoder of another of the VAEs.

The encoder 101 of the structure model 100 can be configured to include, e.g., a plurality of one-dimensional convolutional layers and a plurality of fully connected layers. The encoder 101 receives, as an input, a (M×N)-dimensional structure matrix determinant (structure representation), and converts the (M×N)-dimensional structure matrix determinant to an L-dimensional vector. The decoder 102 can be configured to include, e.g., a plurality of fully connected layers and a RNN (Recurrent Neural Network). The decoder 102 receives, as an input, the L-dimensional vector, and reversely converts the L-dimensional vector to the (M×N)-dimensional structure matrix determinant.

The encoder 105 and the decoder 106 of each of the inner VAEs of the structure-property relationship model 104 can be configured to include, e.g., a plurality of fully connected layers. The encoder 105 receives, as an input, a (L+P)-dimensional vector 107 (referred to also as an extended vector or a structure generation vector) including, as components, the L-dimensional vector corresponding to the latent variable (conversion result) of the structure model 100 (outer VAE) and a P-dimensional vector (target value vector) including an arrangement of P physical property values. The encoder 105 outputs an intermediate vector (latent representation) 108 in a dimension lower than that of the vector 107. The latent space of the structure-property relationship model 104 gives a latent representation in which a combination of a structure feature and a physical property value feature is abstracted.

The decoder 106 receives, as an input, the intermediate vector 108, and outputs a (L+P)-dimensional vector 109. P elements extracted from the (L+P)-dimensional vector 109 are the arrangement of the physical property values. The L-dimensional vector extracted from the output of the decoder 106 is input to the decoder 102 of the structure model 100, and the (M×N)-dimensional structure matrix determinant is output.

For example, the system sequentially inputs chemical structure formulas (structure representation) of known compounds and target physical property values thereof to the trained chemical structure formula generation model 10. Thus, it is possible to generate a novel chemical structure formula expected to show values similar to the target physical property values. Alternatively, the system may also sequentially input combinations of respective chemical structure formulas of higher-performance compounds among the known compounds and predetermined physical property values including values in the vicinity thereof (which are referred to also as target values) to the trained chemical structure formula generation model 10. This can increase a probability that, when values close to the target physical property values are shown, a novel chemical structure formula is generated.

In a task executed by the embodiment in the present description, there are two major learning targets to be acquired by the chemical structure formula generation model. One of the learning targets is grammar rules for a representational form representing a chemical structure formula, and another of the learning targets is a relationship between the chemical structure (chemical structure formula) and a physical property value. In the training of the VAE, a loss function is given such that the input to the encoder and the output of the decoder are equal, and parameters of the encoder and the decoders are updated (optimized).

In the two learning targets described above, the physical property value is required only in the learning of a relationship between a feature and the physical property value. Types of the physical property values include a type representing a physical property and a type representing a chemical property. Either of the types of the physical property values is significantly affected by a local structural feature such as a main-chain structure, a terminal structure, or a partial structure. Accordingly, in the learning of the relationship between the chemical structure and the physical property value, the relationships between the feature values extracted from the chemical structure formula and the physical property values, instead of the chemical structure formula itself, can be used as training data.

The embodiment in the present description mainly executes the following steps. First, the system receives user settings and data to determine a learning model (network structure). Then, the system executes learning by (training of) the chemical structure formula generation model. The learning by the chemical structure formula generation model includes training of the structure model (outer VAE) 100 with catalog data, training of the structure model 100 with a chemical structure formula in experiment data, and training of the structure-property relationship model 104 (the one or more inner VAEs) with the experiment data. The system builds the chemical structure formula generation model from the trained VAEs, and generates the novel chemical structure formula.

First Embodiment

Figure 2:
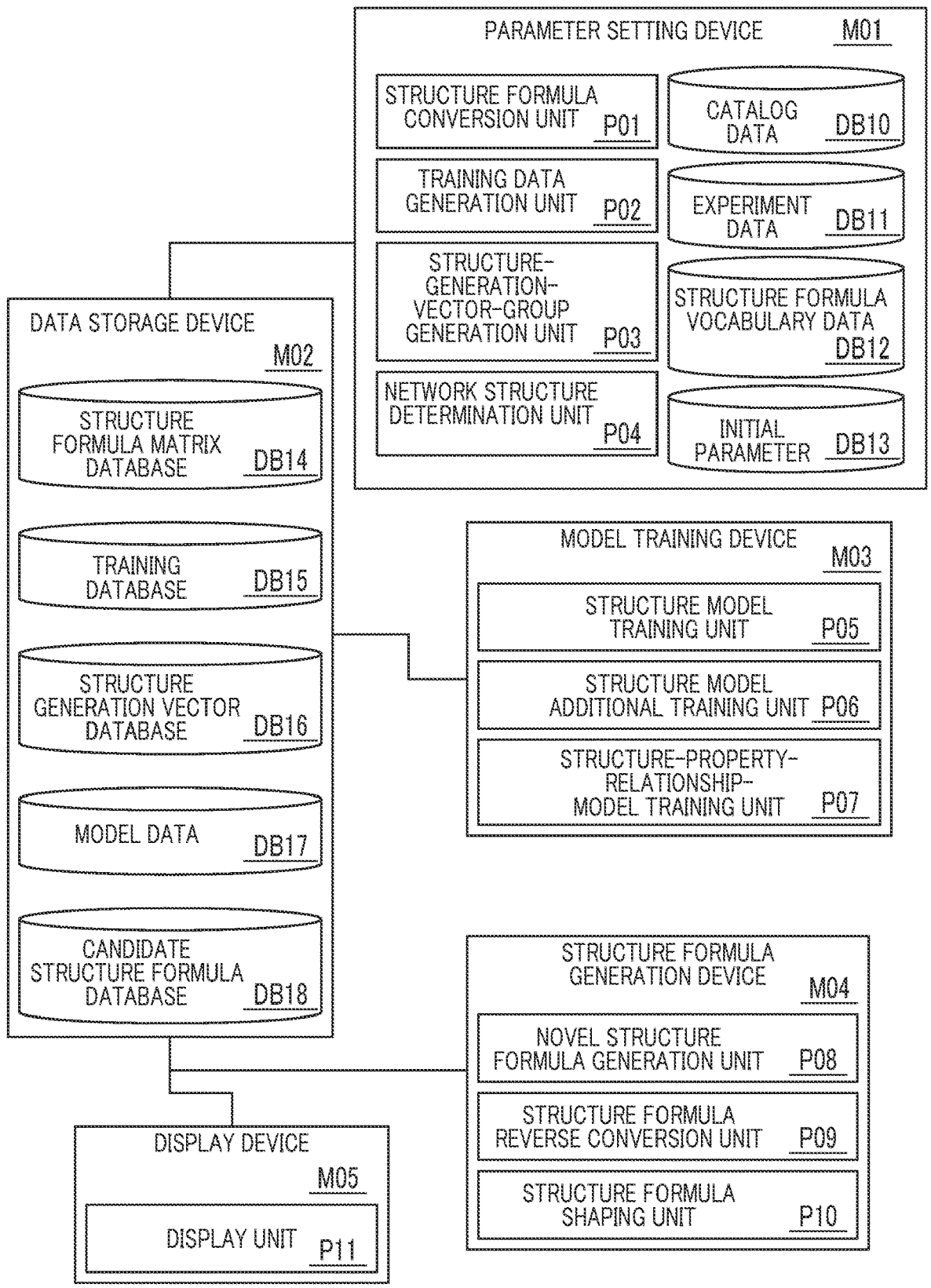
FIG. 2 illustrates an example of a configuration of a chemical structure formula generation system according to the first embodiment.

FIG. 2 illustrates an example of a configuration of a chemical structure formula generation system according to the first embodiment. The present system includes a parameter setting device M01, a data storage device M02, a model training device M03, a structure formula generation device M04, and a display device M05 which are mutually communicative via a network.

The parameter setting device M01 sets or generates various data items including parameters for generation of the chemical structure formula generation system (including training). In the present embodiment, the parameter setting device M01 includes a structure formula conversion unit P01, a training data generating unit P02, a structure-generation-vector-group generation unit P03, and a network structure determination unit P04. These are programs. The parameter setting device M01 further stores a catalog data DB10, an experiment data DB11, a structure formula vocabulary data DB12, and an initial parameter DB13.

The data storage device M02 can store various types of data including data (information) generated by another device. In the present embodiment, the data storage device M02 stores a structure formula matrix database DB14, a training database DB15, a structure generation vector database DB16, a model data DB17, and a candidate structure formula database DB18.

The model training device M03 trains the learning model included in the chemical structure formula generation system. In the present embodiment, the model training device M03 includes a structure model training unit P05, a structure model additional training unit P06, and a structure-property-relationship-model training unit P07. These are programs.

The structure formula generation device M04 uses the trained chemical structure formula generation model to generate (estimate) a chemical structure formula of a novel material expected to a have desired physical property value. In the present embodiment, the structure formula generation device M04 includes a novel structure formula generation unit P08, a structure formula reverse conversion unit P09, and a structure formula shaping unit P10. These are programs.

The display device M05 is capable of presenting information acquired from another device to a user, while receiving input data from the user and transmitting the input data to another device. The display device M05 includes a display unit P11, which is a program.

FIG. 3 illustrates an example of a hardware configuration of the structure formula generation device M04. The structure formula generation device M04 includes a processor U111 having arithmetic performance and a DRAM U112 providing a volatile temporary storage region that stores a program to be executed by the processor U111 and data.

The structure formula generation device M04 further includes a communication device U113 that performs data communication with other devices including another device in the present system, and an auxiliary storage device U114 providing a permanent information storage region using a HDD (Hard Disk Drive), a flash memory, or the like. The structure formula generation device M04 also includes an input device U115 that receives an operation from the user and a monitor U116 (an example of an output device) that presents, to the user an output result in each process.

For example, the auxiliary storage device U114 stores programs such as the novel structure formula generation unit P08, the structure formula reverse conversion unit P09, and the structure formula shaping unit P10. The program to be executed by the processor U111 and data to be processed thereby are loaded from the auxiliary storage device U114 to the DRAM U112.

Respective hardware elements included in the other devices included in the chemical structure formula generation system, specifically the parameter setting device M01, the data storage device M02, the model training device M03, and the display device M05 may be the same as those included in the structure formula generation device M04. It may also be possible to integrate functions distributed to a plurality of devices into one device or distribute the functions of the plurality of devices described above to a larger number of devices. Thus, the chemical structure formula generation system includes one or more storage devices and one or more processors.

FIG. 4 illustrates an example of a configuration of the catalog data DB10. The catalog data DB10 is a database of chemical structure formulas, and includes a large quantity of records. Each of the records stores information about one chemical structure formula. Data in the catalog data DB10 can include, e.g., readily available open data published in a state in which the open data can be freely used for secondary use. In the embodiment in the present description, the chemical structure formula is represented by a character string (representation) according to a SMILES notation.

In the example of the catalog data DB10 illustrated in FIG. 4, a Table ID column T0C1 indicates an identifier of the table (table illustrated in FIG. 4). A Table Type column T0C2 indicates a type of data stored in the table. The Table Type column T0C2 indicates that the present table is a table of catalog data. An ID column T0C3 indicates an identifier of a chemical structure formula. A SMILES column T0C4 indicates a SMILES representation of the chemical structure formula.

FIG. 5 illustrates an example of a configuration of the experiment data DB11. The experiment data DB11 stores experiment data indicating one or more attention-receiving physical property values of the chemical structure formula. Each of records includes a pair of an experiment result of one of the one or more attention-receiving physical property values and information about one chemical structure formula. It is assumed that the number of the records in the experiment data DB11 is smaller than the number of the records in the catalog data DB10.

In the example of the experiment data DB11 illustrated in FIG. 5, a Table ID column T1C1 indicates an identifier of the table (table illustrated in FIG. 5). A Table Type column T1C2 indicates a type of data stored in the table. A Table Type column T1C2 indicates that the present table is a tale of experiment data.

An ID column T1C3 indicates an identifier of a chemical structure formula. A SMILES column T1C4 indicates a SMILES representation of the chemical structure formula. A MWt column T1C5 indicates a molecular weight of a compound represented by the chemical structure formula. A logP column T1C6 indicates a partition coefficient of the compound represented by the chemical structure formula. The molecular weight and the partition coefficient are examples of the physical property values of the chemical structure formula, and the experiment data can include optional physical property values.

FIG. 6 illustrates an example of data included in the structure formula matrix database DB14. The structure formula matrix database DB14 includes a plurality of tables. The structure formula matrix database DB14 is a collection of tables obtained by adding, to each of the tables in the catalog data DB10 and the experiment data DB11, an imparted original data ID and a column of structure formula matrices resulting from conversion of the structure formulas (SMILES). Accordingly, in the first embodiment, the structure formula matrix database DB14 includes the two tables.

The structure formula matrix database DB14 stores the matrices of the chemical structure formulas resulting from the conversion of the SMILES representations by the structure formula conversion unit P01. Thus, in the embodiment in the present description, the character strings representing the chemical structure formulas are converted to the matrices. An ordinate axis of each of the matrices represents a symbol type such as an atomic symbol, while an abscissa axis thereof represents an appearance position.

In the present description, this matrix is referred to as a column formula matrix. When it is assumed that the number of the symbol types is M and a length of the character string representing the chemical structure is N, a structure formula sequence is in an (M×N) dimension. The length of the character string may vary depending on the structure formula. Accordingly, padding is performed using a negative number and a zero value to generate a fixed-strength matrix. The structure formula matrix has information about which symbol appears at which position, and consequently the structure formula is uniquely determined, and it is possible to generate the structure formula by reversely converting the structure formula matrix.

As illustrated in FIG. 6, the structure formula matrix database DB14 includes a catalog-data-structure-formula matrix table 141 and an experiment-data-structure-formula matrix table 142. The catalog-data-structure-formula matrix table 141 is generated from the catalog data DB10, and further has the structure formula matrices added thereto. The experiment-data-structure-formula matrix table 142 is generated from the experiment data DB11, and further has the structure formula matrices added thereto.

In the catalog-data-structure-formula matrix table 141, a Table ID column T3C1 indicates an identifier of the table (table illustrated in FIG. 6). A Table Type column T3C2 indicates a type of data stored in the table. The Table Type column T3C2 indicates that the present table is a table generated from the catalog data. An ID column T3C3 indicates an identifier of a chemical structure formula. A SMILES column T3C4 indicates a SMILES representation of the chemical structure formula. A structure formula matrix column T3C5 indicates a structure formula matrix of the chemical structure formula resulting from conversion of the SMILES representation by the structure formula conversion unit P01.

In the experiment-data-structure-formula matrix table 142, a Table ID column T4C1 indicates an identifier of the table (table illustrated in FIG. 6). A Table Type column T4C2 indicates a type of data stored in the table. The Table Type column T4C2 indicates that the present table is a table generated from the experiment data. An ID column T4C3 indicates an identifier of a chemical structure formula. A SMILES column T4C4 indicates a SMILES representation of the chemical structure formula. A MWt column T4C5 represents a molecular weight of the compound represented by the chemical structure formula. A logP column T4C6 represents a partition coefficient of the compound represented by the chemical structure formula. A structure formula matrix column T4C7 indicates a structure formula matrix of the chemical structure formula resulting from conversion of the SMILES representation by the structure formula conversion unit P01.

FIG. 7 illustrates an example of data included in the training database DB15. The training database DB15 stores data generated from the structure formula matrix database DB14 by the training data generation unit P02 to be used to train the chemical structure formula generation model. The chemical structure formula generation model in the embodiment in the present description includes the structure model and the structure-property relationship model. As illustrated in FIG. 6, the training database DB15 includes a structure model table 151 and a structure-property relationship model table 152. The structure model table 151 stores a structure formula matrix group (compound structure representation group) of compounds unassociated with measurement values of the physical property value. The structure-property relationship model table 152 stores a structure formula matrix group (compound structure representation group) of compounds associated with the measurement values of the physical property value.

An example of the structure model table 151 illustrated in FIG. 7 stores the same information as that stored in the catalog-data-structure-formula matrix table 141 except for a Table ID column T5C1. The Table ID column T5C1 indicates an identifier of the structure model table 151 illustrated in FIG. 7. Columns T5C2 to T5C5 are respectively the same as the columns T3C2 to T3C5 having the same names in the catalog-data-structure-formula matrix table 141.

An example of the structure-property relationship model table 152 illustrated in FIG. 7 stores the same information as that stored in the experiment-data-structure-formula matrix table 142 except for a Table ID column T6C1. The Table ID column T6C1 indicates an identifier of the structure-property relationship model table 152 illustrated in FIG. 6. The columns T6C2 to T6C7 are respectively the same as the columns T4C2 to T4C7 having the same names in the experiment-data-structure-formula matrix table 142.

Figures 8, 9:
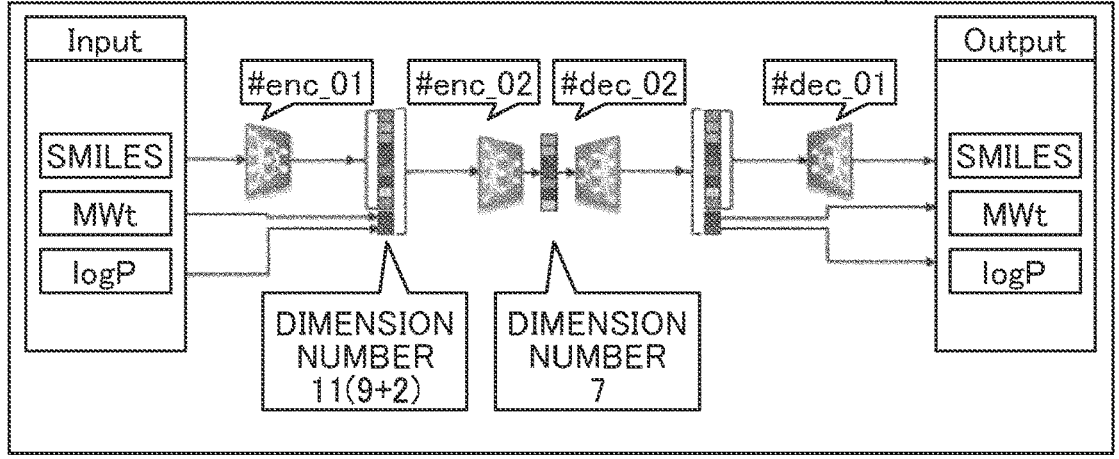
FIG. 8 illustrates an example of information included in initial parameters.
FIG. 9 illustrates an example of a network structure confirmation screen displayed by a display unit for a user in a display device.

FIG. 8 illustrates an example of information included in the initial parameter DB13. The initial parameter DB13 stores all initial values of parameters required to define the network structure. For example, the initial values of structure parameters of the neural networks, the initial values of training parameters, and the initial values of other user setting data are stored. The updated parameters are stored in the model data DB17.

Note that, when default values are given in advance, some of the initial parameters may also be omitted. For example, parameters generally required for a network definition for a neural network, such as types of layers included in the neural network, the number thereof, the order thereof, dimension numbers thereof, weights of neurons, and renewal rates of the weights, may also be omitted.

The user can set the initial parameter DB13 via an input device of any of the devices. The initial parameter DB13 includes information required to configure the chemical structure formula generation model. In an example illustrated in FIG. 8, "CatalogData Tables" indicates the catalog data to be used. "ExperimentData Tables" indicates the experiment data to be used. "Target Properties" indicates types of the attention-receiving physical property values. "Target Property Values" indicates target values of the types of the attention-receiving physical property values.

"Number_of_vae_relation" indicates a stage number of the VAE (inner VAE) of the structure-property relationship model. "VAE_Initial_Params" indicates the initial values of the individual parameters of the VAEs of the chemical structure formula generation model. More specifically, "grammar_layer" indicates a configuration of the structure model such as the number of VAE (outer VAE) layers and the dimension numbers thereof. "vae_relation_layers" indicates a configuration of a structure-property value relationship model such as the number of individual VAE layers thereof and the dimension numbers thereof. "middle_dims" indicates a list of the dimension numbers in intermediate outputs from the encoders or the decoders.

FIG. 9 illustrates an example of a network structure confirmation screen 201 to be displayed by the display unit P11 for the user in the display device M05. The display unit P11 generates a configuration diagram of the chemical structure formula generation model from configuration information of the chemical structure formula generation model received from the network structure determination unit P04, and displays the configuration diagram on the monitor.

In an example of the configuration illustrated in FIG. 9, the structure model corresponding to the outer VAE includes an outer encoder #enc_01 and an outer decoder #dec_01. The structure-property relationship model corresponding to the inner VAE includes an inner encoder #enc_02 and an inner decoder #dec_02. The inner VAE is interposed between the outer encoder #enc_01 and the outer decoder #dec_01.

The outer encoder #enc_01 receives, as an input, the structure formula matrix generated from the SMILES representation, and outputs a nine-dimensional intermediate vector (latent representation). The inner encoder #enc_02 receives, as an input, an eleven-dimensional vector obtained by combining an output of the outer encoder #enc_01 with two physical property values (MWt and logP), and outputs a seven-dimensional intermediate vector (latent representation).

The inner decoder #dec_02 receives, as an input, an output of the inner encoder #enc_02, and outputs an eleven-dimensional vector. This vector is obtained by combining the nine-dimensional vector corresponding to the chemical structure formula with the two-dimensional vector representing the two physical property values. The outer decoder #dec_01 receives, as an input, the nine-dimensional vector extracted from the output of the inner decoder #dec_02, and outputs a vector representing the chemical structure matrix. By reversely converting the chemical structure matrix, it is possible to obtain the SMILES representation of the chemical structure formula.

By referring to the network structure confirmation screen 201, the user can check whether or not a chemical structure formula generation model to be configured has a desired configuration. When desiring a change in the configuration of the chemical structure formula generation model, the user can input data for correction from the input device of the display device M05.

The display unit P11 can display, in addition to the network structure confirmation screen 201, a chemical structure formula newly generated by the chemical structure formula generation model and information related thereto. The user can select, from among the displayed chemical structure formulas, the chemical structure formula to be subjected to actual experiment.

Figures 10, 11:
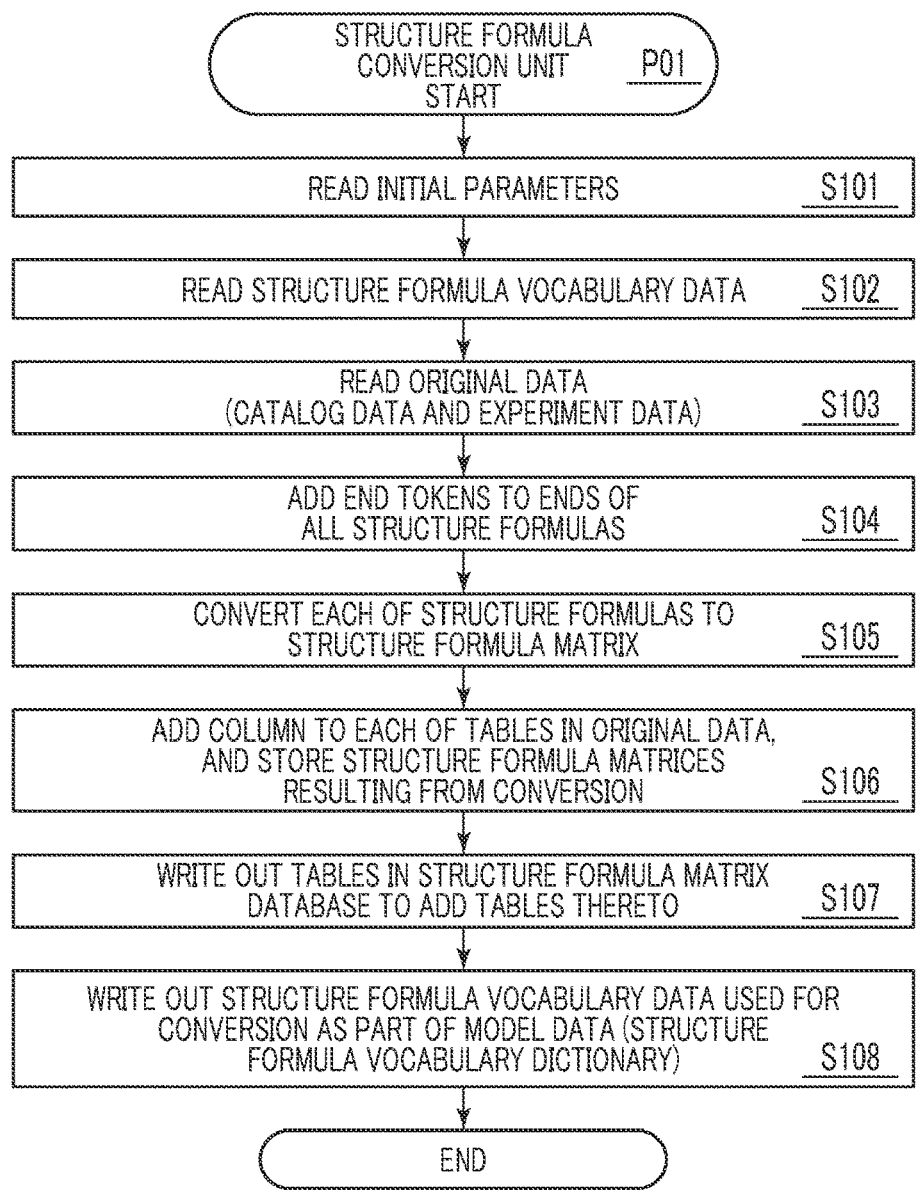
FIG. 10 illustrates an example of a configuration of a model table included in model data.
FIG. 11 illustrates a flow chart of an example of processing by a structure formula conversion unit.

FIG. 10 illustrates an example of a configuration of a model table 171 included in the model data DB17. The model data DB17 stores parameters required to define the network structure of the chemical structure formula generation model. All the parameters including default values not included in the initial parameters are included. For example, the structure parameters of the neural networks, the training parameters, vocabulary data required for reverse conversion of the structure formula matrix, and other user setting data are included. The parameters are sequentially updated as training proceeds. To the model data DB17, reading/writing is performed with timing such as, e.g., when training is started, during the training, or when the training is ended.

The model table 171 is generated in the network structure determination unit P04, and is included in the model data DB17. The model table 171 in FIG. 10 corresponds to a configuration diagram of the chemical structure formula generation model illustrated in FIG. 9. In the example in FIG. 10, a Network ID column T7C1 indicates an identifier of the encoder or decoder of the chemical structure formula generation model. A Network Order column T7C2 indicates the order of the encoder or the decoder counted from the input. A Nest Order column T7C3 indicates the order of the VAE having a nesting structure counted from the input. A Target column T7C4 indicates an identifier of data to be used to train the VAE.

FIG. 11 illustrates a flow chart of an example of processing in the structure formula conversion unit P01. The structure formula conversion unit P01 converts a character string of the chemical structure formula included in each of the catalog data and the experiment data to a structure formula matrix. First, the structure formula conversion unit P01 reads required initial parameters from the initial parameter DB13 (S101). The structure formula conversion unit P01 further reads the structure formula vocabulary data DB12 (S102). The structure formula vocabulary data DB12 associates types of vertically arranged elements in the structure formula matrix with symbols in the SMILES representation. The vertical dimension number and the number of words in the structure formula matrix are equal to each other.

Next, the structure formula conversion unit P01 reads the original data from each of the catalog data DB10 and the experiment data DB11 which are indicated by the initial parameters (S103). The structure formula conversion unit P01 adds an end token to an end of each of all the structure formulas in the read data (S104). The structure formula conversion unit P01 refers to the structure formula vocabulary data DB12, and converts each of all the structure formulas to the structure formula matrix (S105).

The structure formula conversion unit P01 adds a column to each of the tables in the original data, and stores the structure formula matrices resulting from the conversion (S106). Thus, the catalog-data-structure-formula matrix table 141 and the experiment-data-structure-formula matrix table 142 which are illustrated in FIG. 6 are generated. The structure formula conversion unit P01 writes out the generated tables 141 and 142 into the structure formula matrix database DB14 to add the tables 141 and 142 thereto (S107). The structure formula conversion unit P01 further writes out the structure formula vocabulary data used for the conversion as a part (structure formula vocabulary dictionary) of the model data DB17 (S108). The structure formula vocabulary data is referenced to allow the structure formula matrix to be reversely converted and allow the SMILES representations of the chemical structure formulas to be obtained.

Figure 12:
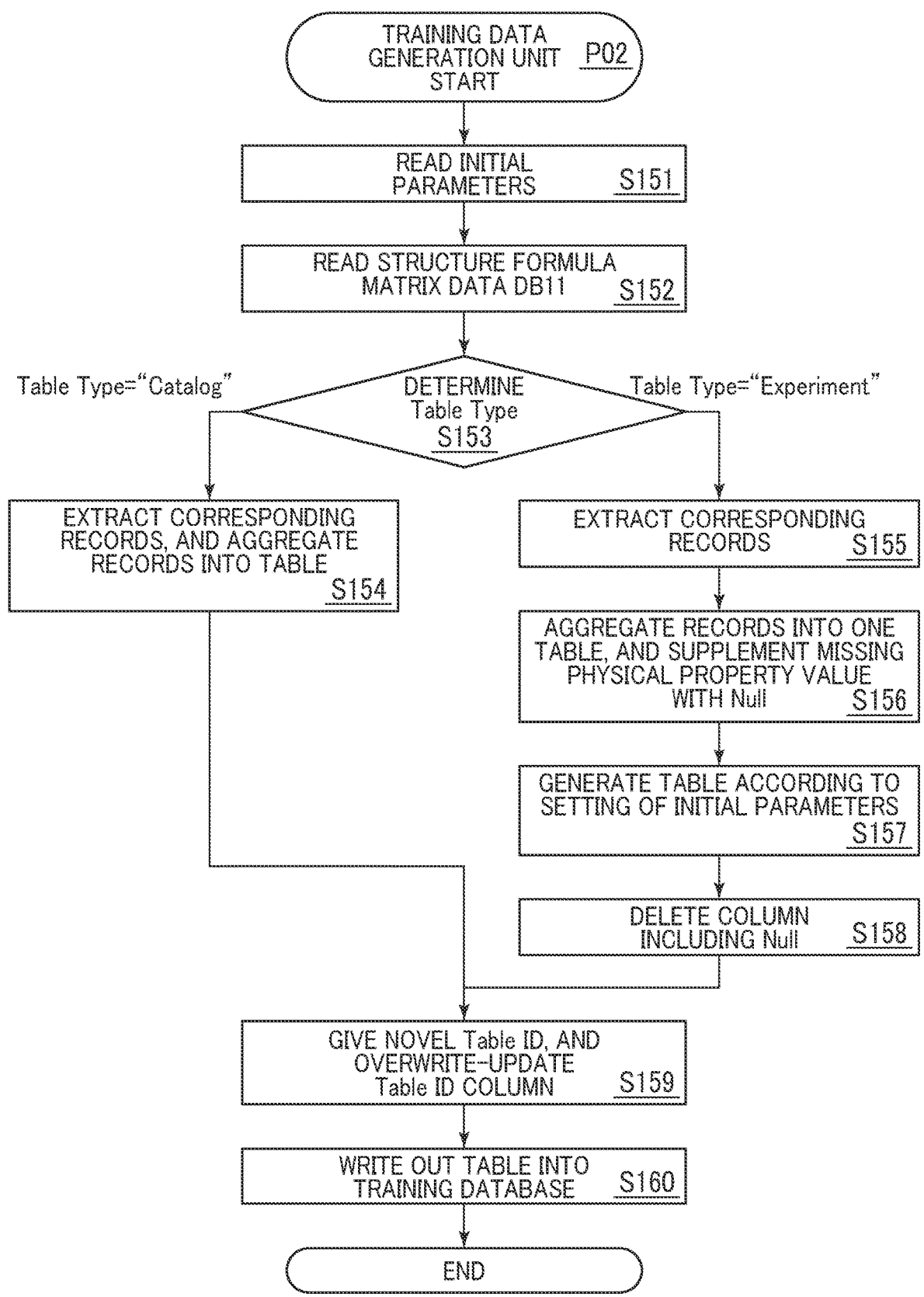
FIG. 12 illustrates a flow chart of an example of processing by a training data generation unit.

FIG. 12 illustrates a flow chart of an example of processing by the training data generation unit P02. The training data generation unit P02 generates the training data for each of the VAEs of the chemical structure formula generation model. First, the training data generation unit P02 reads the required initial parameters from the initial parameter DB13 (S151). Then, the training data generation unit P02 reads the structure formula matrix database DB14 (S152). The training data generation unit P02 determines a Table Type of each of records in the read data (S153).

The training data generation unit P02 executes different processing depending on the Table Type. Processing for the record in which the Table Type is "Catalog" (S153: Catalog) will be described. The training data generation unit P02 extracts the corresponding records, and aggregates the records into one table (S154).

Next, processing for the record in which the Table Type is "Experiment" (S153: Experiment) will be described. The training data generation unit P02 reads the corresponding records (S155), and aggregates the records into one table (S156). When any of the records includes a missing physical property, the training data generation unit P02 supplements a field of the physical property value with Null. The missing physical property value is a physical property value included in any other record and is not included in the record of concern.

Next, the training data generation unit P02 generates the tables according to the stage number of the structure-property relationship model indicated by the initial parameters (S157). Each of the tables stores the training data for the one inner VAE. The training data generation unit P02 deletes the column of the generated table including Null (S158). A physical property value set in the generated table satisfies an inclusion relation described later (see, e.g., the fourth embodiment). The training data generation unit P02 gives a novel Table ID to the generated table, and overwrite-updates the Table ID column (S159). The training data generation unit P02 writes out the generated table into the training database (S160).

Figure 13:
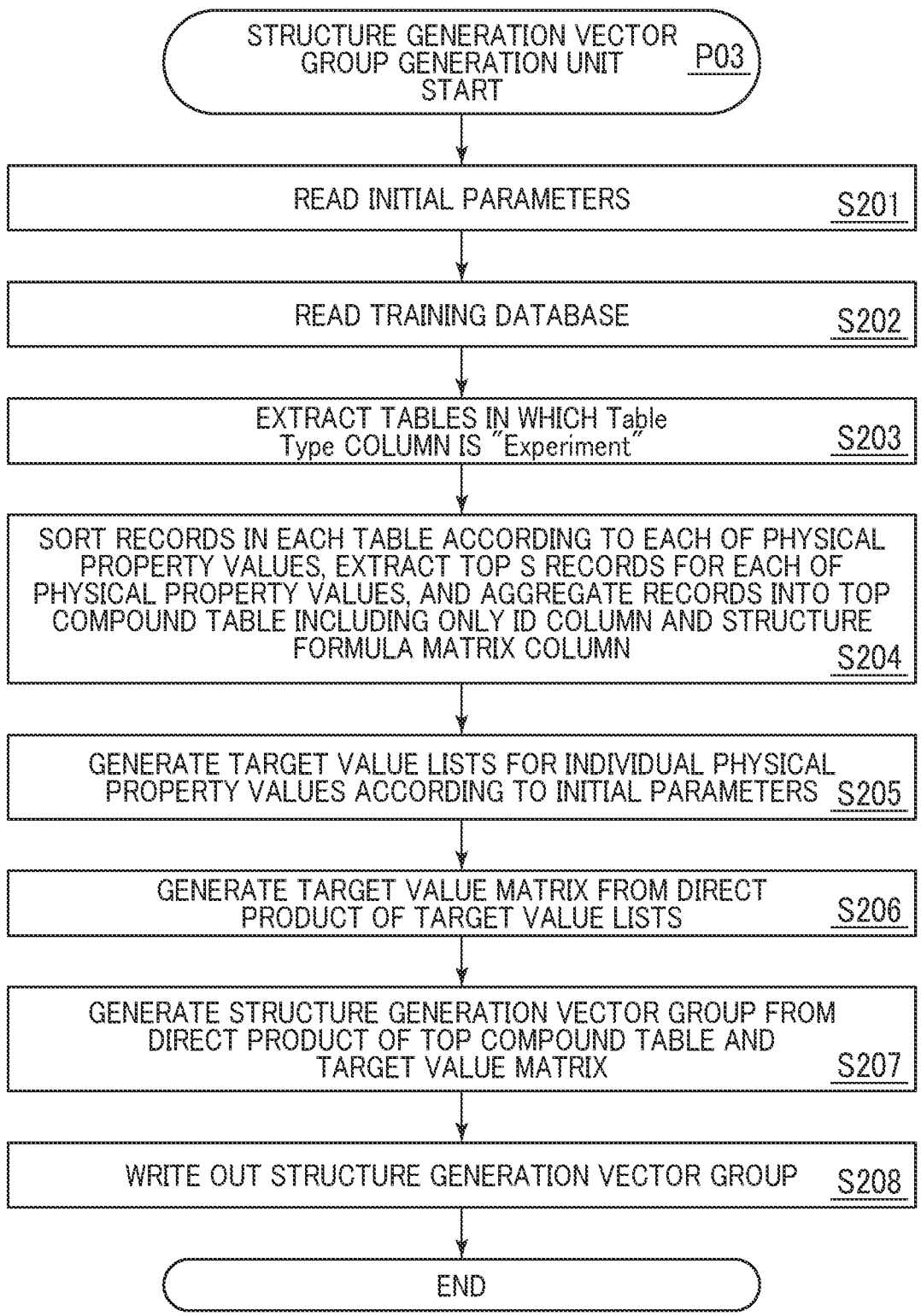
FIG. 13 illustrates a flow chart of an example of processing by a structure-generation-vector-group generation unit.

FIG. 13 illustrates a flow chart of an example of processing by the structure-generation-vector-group generation unit P03. The structure-generation-vector-group generation unit P03 generates input data for generating (estimating) a novel chemical structure formula expected to have a target physical property value after the training of the chemical structure formula generation model.

First, the structure-generation-vector-group generation unit P03 reads the required initial parameters from the initial parameter DB13 (S201). Then, the structure-generation-vector-group generation unit P03 reads the training database DB15 (S202). The structure-generation-vector-group generation unit P03 extracts, from the training database, the tables in which the Table Type is "Experiment" (S203). Each of the tables indicates the training data for the one corresponding inner VAE.

The structure-generation-vector-group generation unit P03 sorts the records in each of the extracted tables according to each of the physical property values, and extracts the top S records for each of the physical property values in each of the tables, where S represents a natural number indicated by the initial parameter. When the table includes a plurality of types of the physical property values, the top S records for each of the physical property value types are extracted. The structure-generation-vector-group generation unit P03 aggregates the extracted records into a top compound table including only an ID column and a structure formula matrix column (S204). Note that, when a plurality of the records each having the same ID have been extracted, only one of those records is stored in the top compound table.

The generation of the top compound table is not limited to the method described above. For example, it may also be possible to extract the records from one of the tables, e.g., the table including the largest number of physical property value types or extract the top records for only the specified physical property value type. The number of the top records to be extracted may also differ from one physical property value type to another.

Then, the structure-generation-vector-group generation unit P03 generates target value lists for the individual physical property values according to the initial parameters (S205). Each of the target value lists indicates a plurality of target values for the corresponding physical property value type. The initial parameters indicate information for generating the plurality of target values, and may also indicate, e.g., the plurality of target values described above, or may also indicate a reference target value or a formula that generates another target value from the number of target values to be generated and the reference target value.

The structure-generation-vector-group generation unit P03 generates a target value matrix from a direct product of the respective target value lists for the individual physical property value types (S206). The structure-generation-vector-group generation unit P03 further generates a structure generation vector group from a direct product of the top compound table and the target value matrix (S207). The structure-generation-vector-group generation unit P03 writes out the generated structure generation vector group into the structure generation vector database DB16 (S208).

Figure 14:
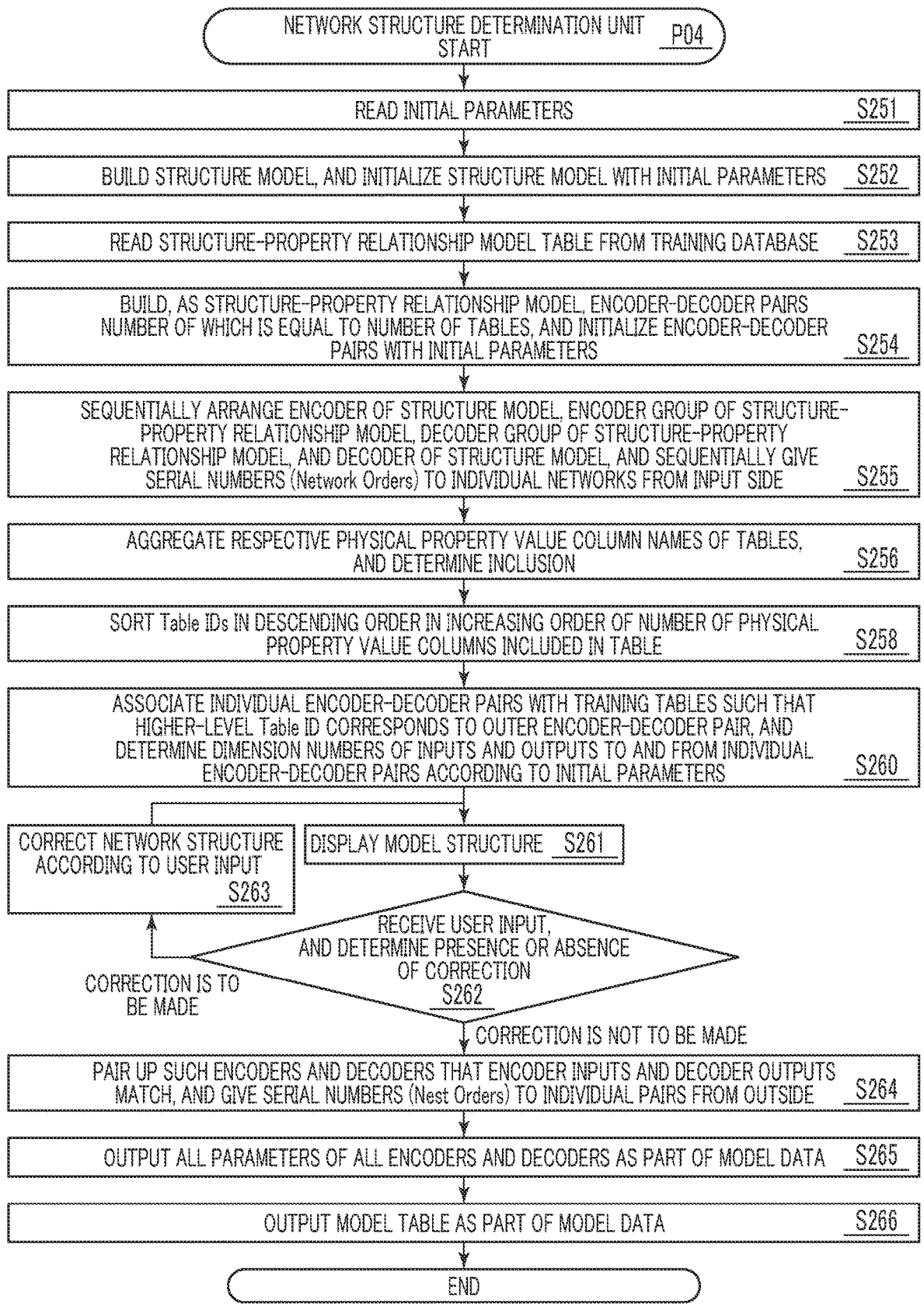
FIG. 14 illustrates a flow chart of an example of processing by a network structure determination unit.

FIG. 14 illustrates a flow chart of an example of processing by the network structure determination unit P04. The network structure determination unit P04 determines a structure of the chemical structure formula generation model (generation of model data) from the initial parameters, the physical property value to be considered x included in the experiment data, or the like.

First, the network structure determination unit P04 reads the required initial parameters from the initial parameter DB13 (S251). The initial parameters to be read include a catalog data identifier, an experiment data identifier, a column name of the target physical property, a dimension number list, and the like.

Next, the network structure determination unit P04 builds a structure model and initializes the structure model with the initial parameters (S252). The network structure determination unit P04 reads the structure-property relationship model table from the training database DB15 (S253). The network structure determination unit P04 builds, as structure-property relationship models, encoder-decoder pairs (inner VAEs) the number of which is equal to the number of the structure-property relationship model tables, and initializes the encoder-decoder pairs with the initial parameters (S254).

The network structure determination unit P04 sequentially arranges the encoder of the structure model, an encoder group of the structure-property relationship models, a decoder group of the structure-property relationship models, and the decoder of the structure model, and sequentially gives serial numbers (Network Orders) to the individual networks from an input side (S255).

The network structure determination unit P04 aggregates respective physical property value column names (physical property value types) of the structure-property relationship model tables and determines inclusion (S256). Between any two of the structure-property relationship model tables, an inclusion relation between the physical property value column names is established. Specifically, the table having a larger number of the physical property value columns includes all the physical property value column names of the table having a smaller number of the physical property value column names. The structure-property relationship model tables are prepared by the training data generation unit P02 such that such an inclusion relation is established.

The network structure determination unit P04 sorts the Table IDs in descending order in increasing order of the number of the physical property value columns included in the table (S258). The network structure determination unit P04 associates the individual encoder-decoder pairs with the training tables such that the higher-level Table IDs correspond to the outer encoder-decoder pairs in the structure-property value relationship model. The network structure determination unit P04 determines the dimension numbers of inputs and outputs to and from the individual encoder-decoder pairs according to the initial parameters (S260).

Then, the network structure determination unit P04 displays a model structure (S261). Specifically, the network structure determination unit P04 transmits information about the model structure to the display unit P11. The display unit P11 generates a structure image of the chemical structure formula generation model according to the received information, and displays the structure image.

The network structure determination unit P04 receives a user input about the structure of the chemical structure formula generation model via the display unit P11, and determines the presence or absence of correction of the network structure (S262).

When receiving a user instruction to correct the network structure (CORRECTION IS TO BE MADE in S262), the network structure determination unit P04 corrects the network structure according to the user input (S263), and displays the corrected network structure by using the display unit P11.

When there is no need to correct the network structure (CORRECTION IS NOT TO BE MADE in S262), the network structure determination unit P04 pairs up such encoders and decoders that encoder inputs and decoder outputs match, and gives serial numbers (Nest Orders) to the individual pairs in order from the outside in (S264). The individual pairs form the VAEs.

The network structure determination unit P04 outputs all the parameters of all the encoders and the decoders as a part of the DB17 to the data storage device M02 (S265). In addition, the network structure determination unit P04 outputs the model table 171 as a part of the model data DB17 to the data storage device M02 (S266).

Figure 15:
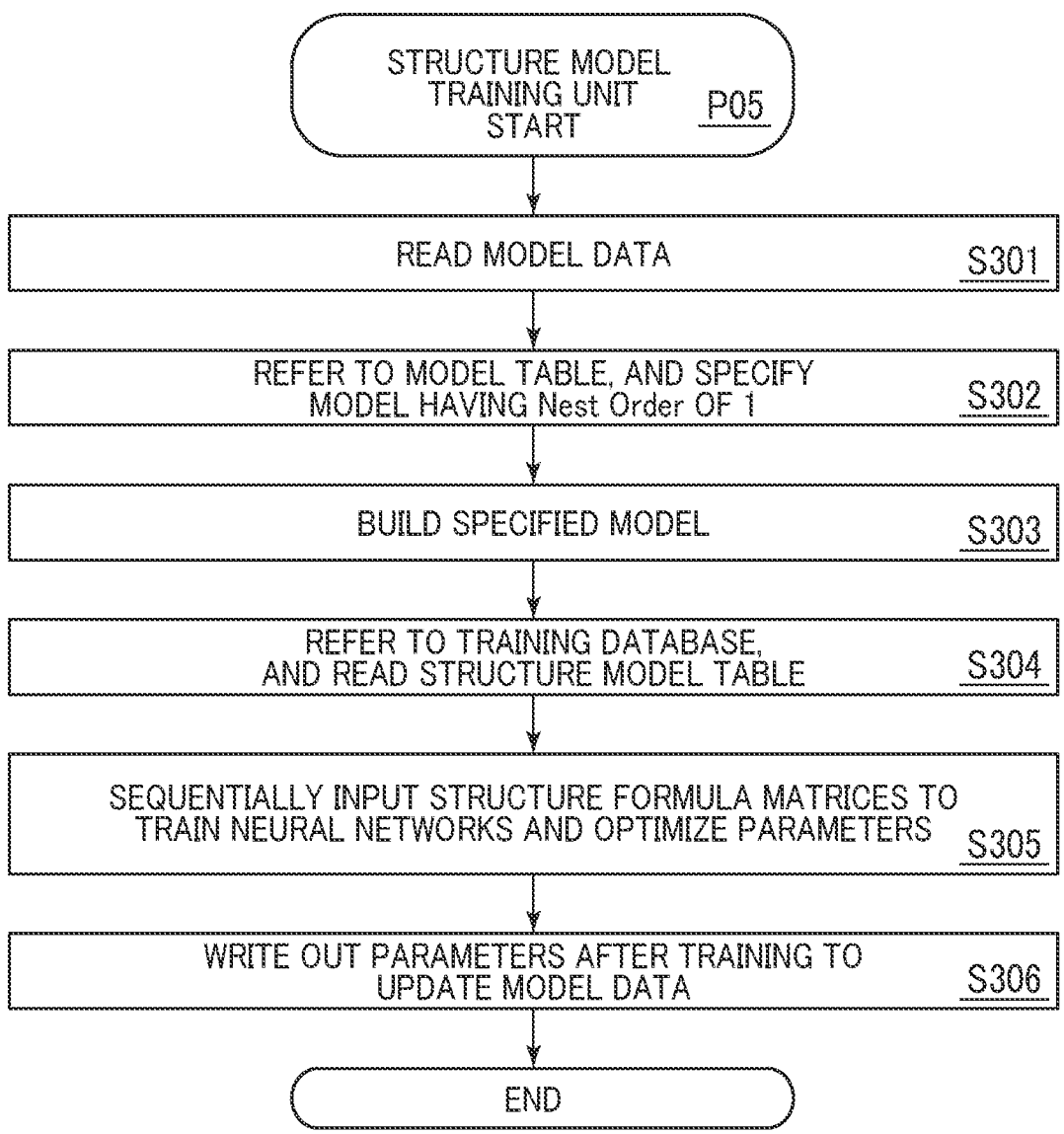
FIG. 15 illustrates a flow chart of an example of processing by a structure model training unit.

FIG. 15 illustrates a flow chart of an example of processing by the structure model training unit P05. The structure model training unit P05 uses the structure model table generated from the catalog data to cause the structure model (outer VAE) to perform learning (referred to also as training). The catalog data DB10 stores a larger number of records (data) than those stored in the experiment data DB11. When the data includes only the chemical structure formulas, a larger amount of data can be prepared as training data, and therefore it is possible to effectively train the entire chemical structure formula generation model.

First, the structure model training unit P05 reads the model data DB17 (S301). Then, the structure model training unit P05 refers to the model table, and specifies a model having the Nest Order of 1 (S302). The model having the Nest Order of 1 is an outermost structure model. The structure model training unit P05 further builds the specified model (S303).

The structure model training unit P05 refers to the training database DB15 to read the structure model table (S304). The structure model training unit P05 sequentially inputs the structure formula matrices to the structure model to train the neural networks (S305). The structure model training unit P05 writes the parameters after the training to update the model data DB17 (S306).

Figure 16:
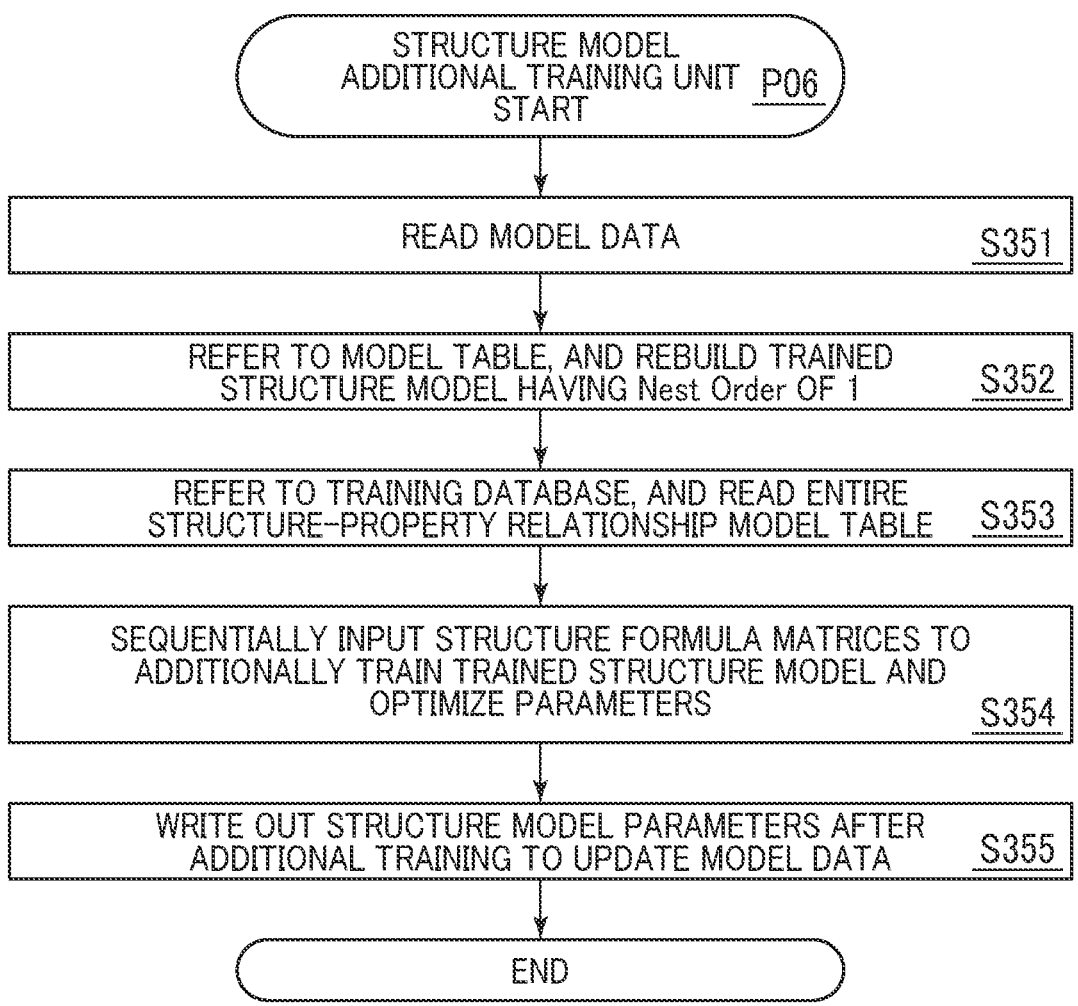
FIG. 16 illustrates a flow chart of an example of processing by a structure model additional training unit.

FIG. 16 illustrates a flow chart of an example of processing by the structure model additional training unit P06. Additional training of the structure model can increase accuracy of feature extraction by the structure model. The structure model additional training unit P06 uses the structure formula matrices in the structure-property relationship model table to additionally train the structure model. First, the structure model additional training unit P06 reads the model data DB17 (S351).

Then, the structure model additional training unit P06 refers to the model table, and rebuilds the trained structure model having the Nest Order of 1 (S352). The structure model additional training unit P06 refers to the training database DB15, and reads the entire structure-property relationship model table (S353).

The structure model additional training unit P06 sequentially inputs the structure formula matrices in the structure-property relationship model table to the structure model to additionally train the trained structure model. The structure model additional training unit P06 updates and optimizes the parameters of the network (S354). The structure model additional training unit P06 writes out parameters of the structure model after the additional training to update the model data DB17 (S355).

Figure 17:
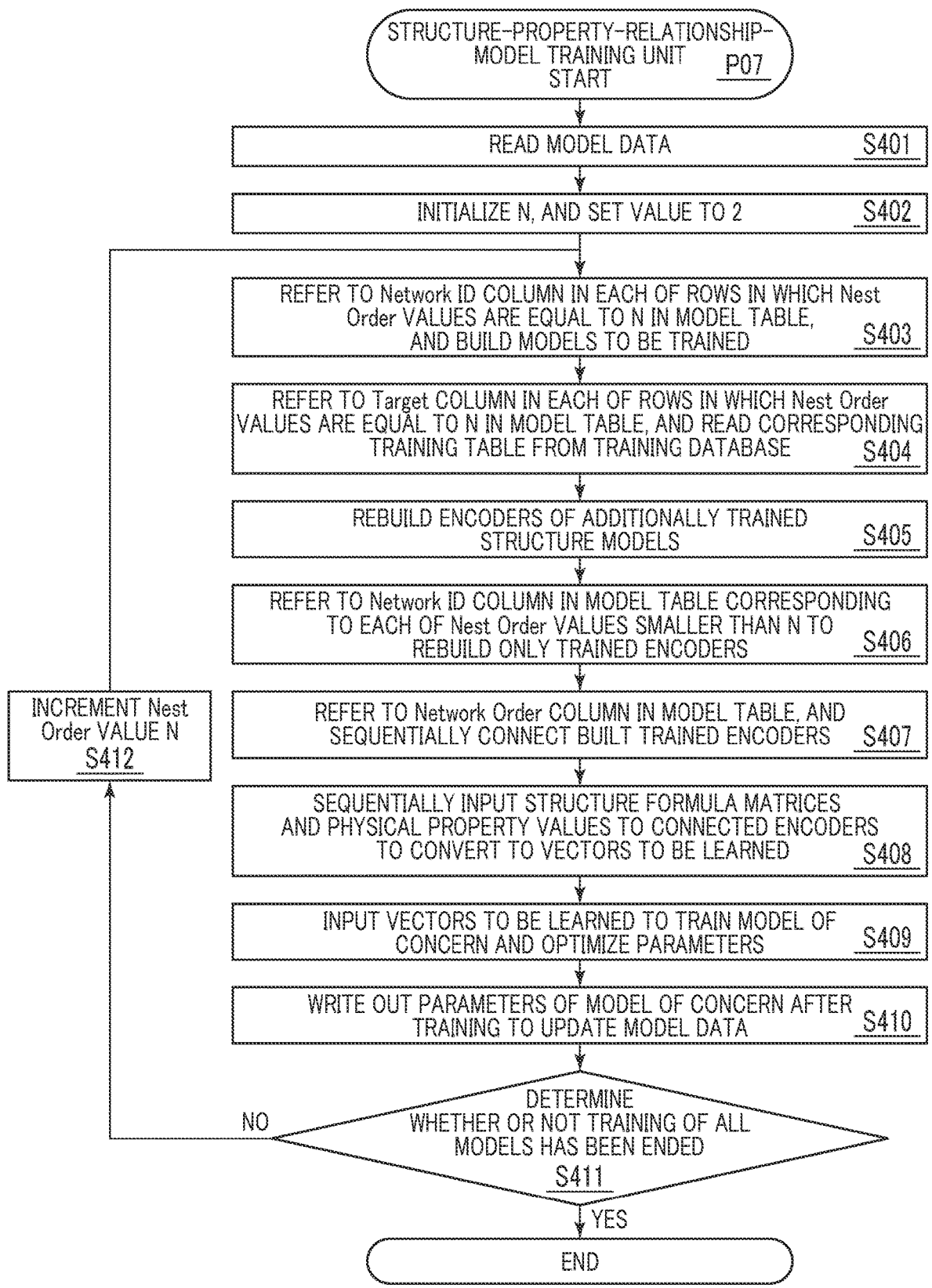
FIG. 17 illustrates a flow chart of an example of processing by a structure-property-relationship-model training unit.

FIG. 17 illustrates a flow chart of an example of processing by the structure-property-relationship-model training unit P07. The structure-property-relationship-model training unit P07 trains each of the VAEs (hereinafter referred to also as models) in the structure-property relationship model. For the training of the inner VAEs, all the encoders outside the inner VAEs are rebuilt and connected.

First, the structure-property-relationship-model training unit P07 reads the model data DB17 (S401). The structure-property-relationship-model training unit P07 initializes N and sets a value thereof to 2 (S402). The structure-property-relationship-model training unit P07 refers to the Network ID column in each of rows in which Nest Order values are equal to N, and builds the VAEs of the model to be trained (S403).

The structure-property-relationship-model training unit P07 refers to the Target column in each of the rows in which the Nest Order values are equal to N, and reads, from the training database DB15, the corresponding training table (structure-property relationship model table) (S404).

The structure-property-relationship-model training unit P07 rebuilds only the encoders of the additionally trained structure models (without building the decoders) (S405). In addition, the structure-property-relationship-model training unit P07 refers to the Network ID column in the model table corresponding to each of Nest Order values smaller than N to rebuild only the trained encoders (without building the decoders) (S406). The structure-property-relationship-model training unit P07 refers to the Network Order column in the model table, and sequentially connects the built trained encoders (S407).

The structure-property-relationship-model training unit P07 sequentially inputs, to each of the connected encoders, the structure formula matrices and the physical property values corresponding thereto to perform conversion to vectors to be learned (S408). To the structure model, only the structure formula matrices are input. The structure-property-relationship-model training unit P07 inputs the vectors to be learned to the VAEs each corresponding to the model to be trained to train the model of concern and optimize the parameters of the network (S409). When N=2 is satisfied, the vectors to be learned are vectors obtained by combining results of conversion of the structure matrices of the structure model with physical property value vectors. The structure-property-relationship-model training unit P07 writes out the parameters of the model of concern after the training to update the model data DB17 (S410).

The structure-property-relationship-model training unit P07 determines whether or not training of all the models (VAEs) of the structure-property relationship model has been ended (S411). When the untrained model remains (NO in S411), the structure-property-relationship-model training unit P07 increments the Nest Order value N (S412), and returns to Step S403. When the training of all the models of the structure-property relationship model has been ended (YES in S411), the present flow is ended.

FIG. 18 illustrates a flow chart of an example of processing by the novel structure formula generation unit P08. The novel structure formula generation unit P08 uses the trained chemical structure formula generation model to generate (estimate) candidates for a novel chemical structure formula expected to have a desired physical property value.

First, the novel structure formula generation unit P08 reads the model data DB17 (S451). The novel structure formula generation unit P08 rebuilds the trained structure model and structure-property value relationship model to configure the chemical structure formula generation model (generator) (S452). The novel structure formula generation unit P08 reads the structure generation vector group from the structure generation vector database DB16 (S453).

The novel structure formula generation unit P08 inputs the structure generation vector group to the chemical structure formula generation model to generate the structure formula matrices (S454). The novel structure formula generation unit P08 collectively writes out the structure formula matrices as candidate structure formulas into the candidate structure formula database DB18 (S455).

FIG. 19 illustrates a flow chart of an example of processing by the structure formula reverse conversion unit P09. The structure formula reverse conversion unit P09 converts the structure formula matrices output from the chemical structure formula generation model to SMILES representations (character strings) of the structure formulas.

First, the structure formula reverse conversion unit P09 reads the structure formula vocabulary dictionary from the model data DB17 (S501). The structure formula reverse conversion unit P09 reads the candidate structure formula database DB18 (S502). The structure formula reverse conversion unit P09 converts the structure formula matrices to the structure formulas (SMILES representations) (S503). The structure formula reverse conversion unit P09 deletes the end tokens from the ends (S504). The structure formula reverse conversion unit P09 overwrites the structure formulas in the candidate structure formula database 18DB (S505).

Figure 20:
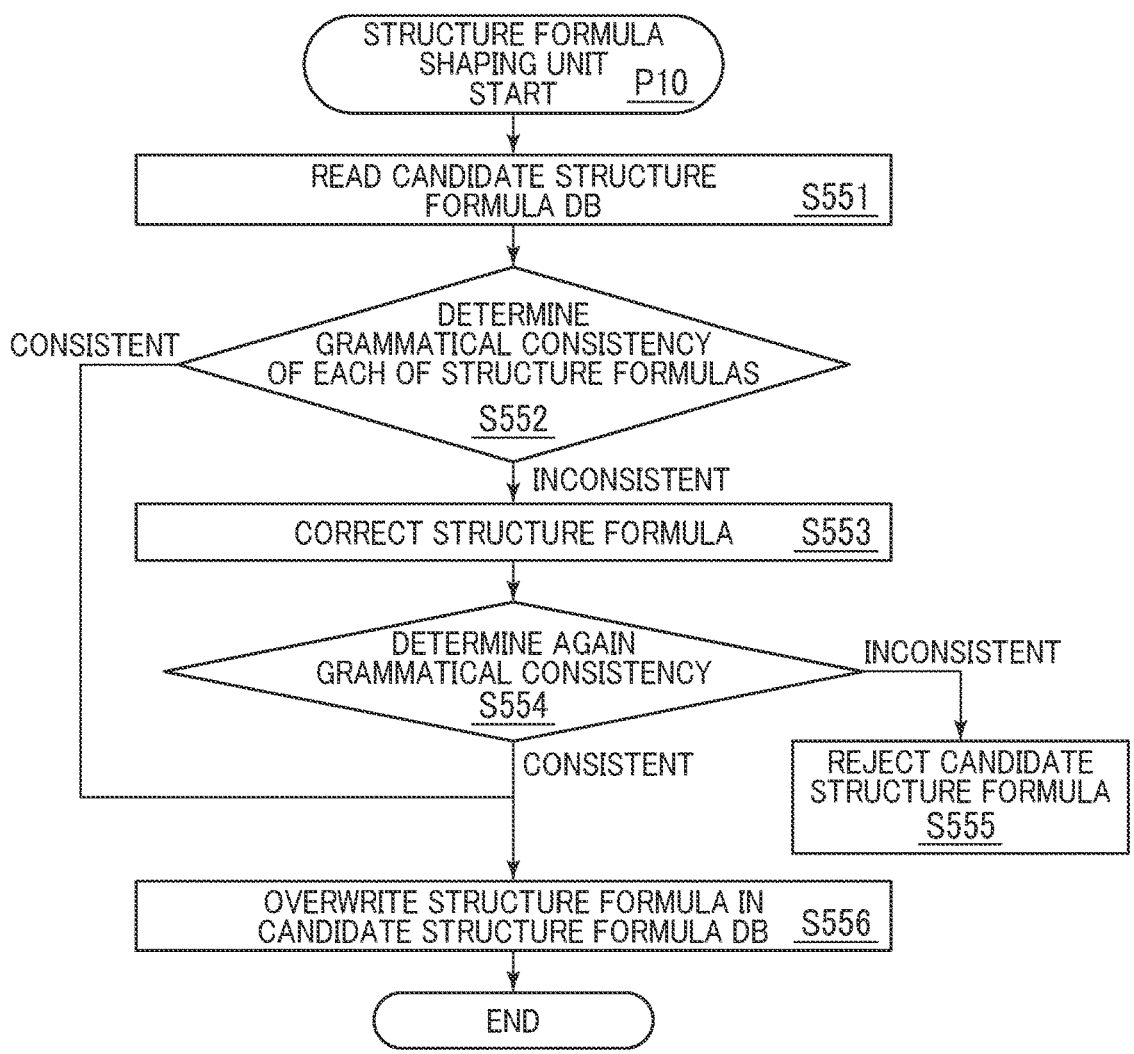
FIG. 20 illustrates a flow chart of an example of processing by a structure formula shaping unit.

FIG. 20 illustrates a flow chart of an example of processing by the structure formula shaping unit P10. Due to properties of the VAEs, the chemical structure formulas generated by the chemical structure formula generation model may include chemical structure formulas not conforming to the grammar of the SMILES. The structure formula shaping unit P10 corrects the chemical structure formulas not conforming to the grammar of the SMILES, and further removes the uncorrectable chemical structure formulas.

First, the structure formula shaping unit P10 reads the candidate structure formula database 18DB (S551). The structure formula shaping unit P10 determines grammatical consistency of each of the chemical structure formulas (S552). When the chemical structure formula does not satisfy the grammatical consistency, the structure formula shaping unit P10 corrects the chemical structure formula (S553). The structure formula shaping unit P10 determines again grammatical consistency of the corrected chemical structure formula (S554). The structure formula shaping unit P10 rejects the candidate structure formula (S555). The structure formula shaping unit P10 overwrites the corrected chemical structure formula in the candidate structure formula database 18DB (S556).

Thus, a chemical structure generation model having the nesting structure can present candidates for a compound having a physical property value more excellent than the physical property value included in the training data, and can generate a chemical structure formula by using a small amount of experiment data. In addition, by additional training of the structure model using the experiment data, it is possible to further increase accuracy of the feature detection by the structure model.

Second Embodiment

The following will describe the second embodiment. A description will be given mainly of a point different from that in the first embodiment. A structure-property value relationship model according to the second embodiment has a nesting structure including multi-stage VAEs. In addition, an input to each of the encoders (each of VAEs) of the structure-property value relationship model is a vector obtained by combining an intermediate vector from the previous-stage encoder with a single physical property value. The structure-property value relationship model including the multi-stage VAEs allows, e.g., a physical property value preferred to be separated to be included in an input to the different VAE.

In the second embodiment, it is assumed that each of all the chemical structure formulas (records) in the experiment data to be used for training has experiment data of a common physical property value type (physical property value name) (the experiment data has no loss). The following will describe an example in which, with each of the chemical structure formulas, experiment data including two types of physical property values MWt and logP is associated.

Figure 21:
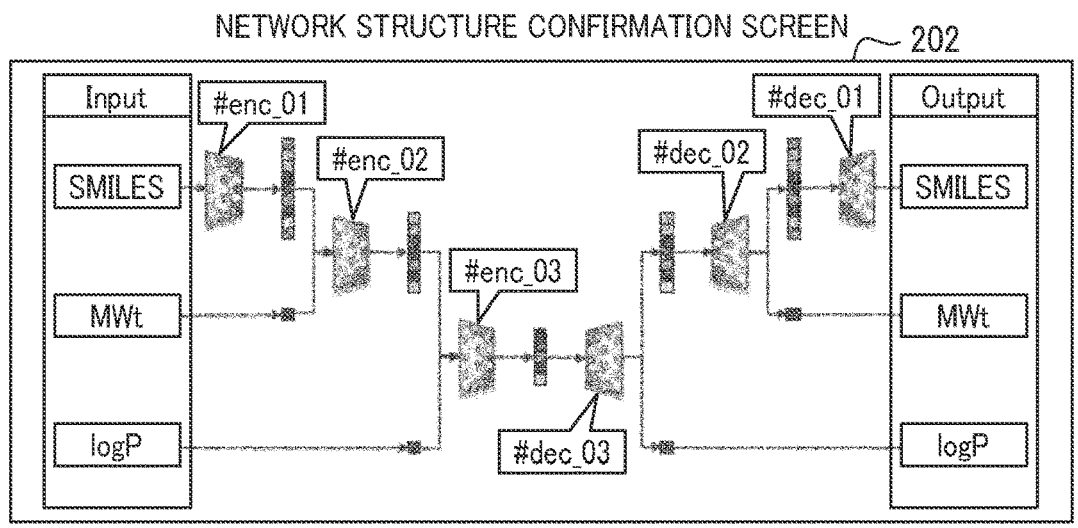
FIG. 21 illustrates an example of a network structure confirmation screen displayed by the display unit for the user in the display device.

FIG. 21 illustrates an example of a network structure confirmation screen 202 displayed by the display unit P11 for the user in the display device M05 according to the second embodiment. The display unit P11 generates a configuration diagram of a chemical structure formula generation model from configuration information of the chemical structure formula generation model received from the network structure determination unit P04, and displays the configuration diagram on the monitor.

In the example of the configuration illustrated in FIG. 21, the structure model corresponding to the outer VAE includes the outer encoder #enc_01 and the outer decoder #dec_01. The structure-property relationship model includes the two inner VAEs. One of the inner VAEs includes the inner encoder#enc_02 and the inner decoder #dec_02. Another of the inner VAEs includes an inner encoder#enc_03 and an inner decoder #dec_03.

The inner encoder #enc_03 and the inner decoder #dec_03 are interposed between the inner encoder #enc_02 and the inner decoder #dec_02. The inner encoder #enc_03, the inner decoder #dec_03, the inner encoder #enc_02, and the inner decoder #dec_02 are interposed between the outer encoder #enc_01 and the outer decoder #dec_01.

The outer encoder #enc_01 receives, as an input, the structure formula matrix generated from the SMILES representation, and outputs the intermediate vector (latent representation). The inner encoder #enc_02 receives, as an input, a vector obtained by combining the output of the outer encoder #enc_01 with a one-dimensional vector representing one physical property value (MWt), and outputs the intermediate vector (latent representation). The inner encoder #enc_03 receives, as an input, a vector obtained by combining the output of the inner encoder #enc_02 with a one-dimensional vector representing one physical property value (logP), and outputs the intermediate vector (latent representation).

The inner decoder #dec_03 receives, as an input, the output of the inner encoder #enc_03, and outputs a vector. A part of the vector corresponds to the input to the inner encoder #enc_03, while another part thereof corresponds to the physical property value (logP). A vector obtained by removing the physical property value vector from the output vector from the inner decoder #dec_03 is input to the inner decoder #dec_02. A part of the vector output from the inner decoder #dec_02 is the input to the inner encoder #enc_02, i.e., the feature vector of the chemical structure formula (chemical structure matrix), while another part thereof is the physical property value vector of the physical property value (MWt).

A vector obtained by removing the physical property value vector from the output vector from the inner decoder #dec_02 is input to the outer decoder #dec_01. The outer decoder #dec_01 outputs a vector representing the chemical structure matrix. By reversely converting the chemical structure matrix, it is possible to obtain the SMILES representation of the chemical structure formula.

FIG. 22 illustrates an example of data included in the training database DB15 according to the second embodiment. FIG. 22 illustrates structure-property relationship model training data. The training data for the structure-property relationship model stores a training table 153 for the outer first VAE (#enc_02 and #dec_02) in the structure-property relationship model and a training table 154 for the inner second VAE (#enc_03 and #dec_03) in the structure-property relationship model.

The first VAE training table 153 has a structure obtained by removing the logP column T6C6 from the structure-property relationship model table 152 illustrated in FIG. 7. A Table ID column T8C1 indicates an identifier of the first VAE training table 153. Columns T8C2 to T8C5 and T8C7 of the first VAE training table 153 store the same information as that stored in the columns T6C2 to T6C5 and T6C7 of the structure-property relationship model table 152. A physical property value required to train the first VAE (#enc_02 and #dec_02) is only MWt included in an input to the first VAE and an output thereof.

The second VAE (#enc_03 and #dec_03) training table 154 has the same structure as that of the structure-property relationship model table 152 illustrated in FIG. 7. A table ID column T9C1 indicates an identifier of the second VAE training table 154. Columns T9C2 to T9C7 of the second VAE training table 154 store the same information as that stored in the columns T6C2 to T6C7 of the structure-property relationship model table 152.

To train the second VAE, it is necessary to rebuild and connect the outer two encoders #enc_01 and #enc_02 to each other. Accordingly, training data includes, in addition to logP corresponding to the input/output physical property value of the second VAE, MWt corresponding to the input physical property value of the encoder #enc_02.

In an example, training data for the first VAE is larger in amount than the training data for the second VAE. The first VAE disposed outside the second VAE has a larger dimension number, and therefore the training of the structure-property relationship model can effectively be performed. This point is the same as in the following third and fourth embodiments.

Figures 23, 24:
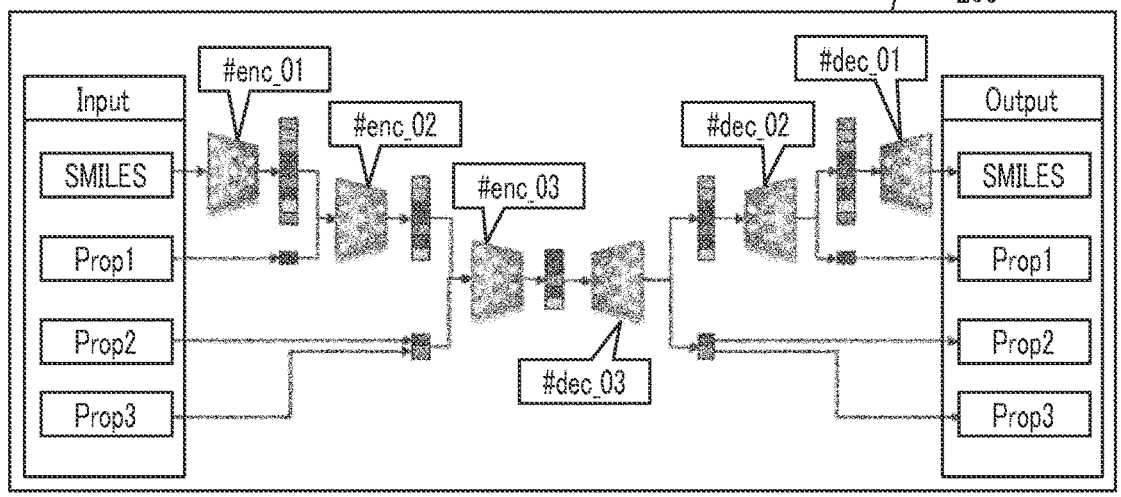
FIG. 23 illustrates an example of a configuration of the model table included in the model data according to the second embodiment.
FIG. 24 illustrates an example of a network structure confirmation screen displayed by the display unit for the user in the display device according to the third embodiment.

FIG. 23 illustrates an example of a configuration of a model table 172 included in the model data DB17 according to the second embodiment. The model table 172 in FIG. 23 corresponds to the configuration diagram of the chemical structure formula generation model illustrated in FIG. 21. In the example in FIG. 23, a Network ID column T10C1 indicates respective identifiers of three encoders and three decoders of the chemical structure formula generation model. A Network Order column T10C2 indicates respective orders of the three encoders and the three decoders from the input. A Nest Order column T10C3 indicates respective orders of three VAEs including the encoders and the decoders from the respective inputs (from the outside). A Target column T10C4 indicates identifiers and target physical property values of data to be used to train the VAEs.

Third Embodiment

The following will describe the third embodiment. A description will be given mainly of a point different from that in the first and second embodiments. A structure-property value relationship model according to the third embodiment has a nesting structure including multi-stage VAEs. In addition, an input to each of the encoders (individual VAEs) of the structure-physical property value relationship model is a vector obtained by combining an intermediate vector from the previous-stage encoder with a single or a plurality of physical proper values. The structure-property value relationship model including the multi-stage VAEs allows, e.g., a physical property value preferred to be combined to be included in the same VAE and allows a physical property value preferred to be separated to be included in an input to the different VAE.

In the third embodiment, it is assumed that each of all the chemical structure formulas (records) in the experiment data to be used for training has experiment data of a common physical property type (physical property value name) (the experiment data has no loss). The following will describe an example in which, with the individual chemical structure formulas, experiment data of three types of physical property values Prop1, Prop2, and Prop3 are associated.

FIG. 24 illustrates an example of a network structure confirmation screen 203 displayed by the display unit P11 for the user in the display device M05 according to the third embodiment. The display unit P11 generates a configuration diagram of a chemical structure formula generation model from configuration information of the chemical structure generation model received from the network structure determination unit P04, and displays the configuration diagram on the monitor.

A network structure illustrated in FIG. 24 is different from the network structure illustrated in FIG. 21 in the second embodiment in that the number of the physical property values in the innermost VAE (#enc_03 and #dec_03) is 2. An input/output physical property value of the outer VAE (#enc_02 and #dec_02) in the structure-property relationship model is Prop1, while input/output physical property values of the innermost VAE (#enc_03 and #dec_03) are Prop1 and Prop2.

FIG. 25 illustrates an example of data included in the training database DB15 according to the third embodiment. FIG. 25 illustrates structure-property relationship model training data The training data for the structure-property relationship model stores a training table 155 for the first VAE (#enc_02 and #dec_02) in the structure-property relationship model and a training table 156 for the second VAE (#enc_03 and #dec_3) in the structure-property relationship model.

The first VAE training table 155 has the same structure as that of the first VAE training table 153 illustrated in FIG. 22. Column names of columns T11C1 to T11C4 and T11C7 are the same as in the first VAE training table 153. A Prop1 column T11C5 indicates a measurement value of Prop1 in each of the chemical structure formulas. A physical property value required to train the first VAE (#enc_02 and #dec_02) is only Prop1 included in the input to the first VAE and in the output thereof.

The second VAE (#enc_03 and #dec_03) training table 156 has a structure obtained by adding two physical property value columns to the first VAE training table 155 illustrated in FIG. 25. Information in columns T12C1 to T12C5 and T12C8 is the same as that in the columns T11C1 to T11C5 and T11C7 of the first VAE training table 155. The added Prop2 column T12C6 and Prop3 column T12C7 indicate respective experiment measurement values of Prop2 and Prop3 in the individual chemical structure formulas.

To train the second VAE, it is necessary to rebuild and connect the outer two encoders #enc_01 and #enc_02 to each other. Accordingly, training data includes, in addition to Prop2 and Prop3 corresponding to the input/output physical property values of the second VAE, Prop1 corresponding to the input physical property value of the encoder #enc_02.

FIG. 26 illustrates an example of a configuration of a model table 173 included in the model data DB17 according to the third embodiment. The model table 173 in FIG. 26 corresponds to the configuration diagram of the chemical structure formula generation model illustrated in FIG. 24. Information in columns T13C1 to T13C3 is the same as the information in the columns T10C1 to T10C3 of the model table 172 according to the second embodiment. A Target column T13C5 indicates an identifier and target physical property values of data to be used to train the VAEs in the present embodiment.

Fourth Embodiment

The following will describe the fourth embodiment. A description will be given mainly of a point different from that in the other embodiments described above. Experiment data in the present embodiment includes a chemical structure formula with a missing physical property value that has been obtained by experiment. By configuring training data to be applied to each of the VAEs in a nesting structure from the experiment data depending on a combination of physical property values associated with each other, more appropriate training is possible.

Figures 27, 28:
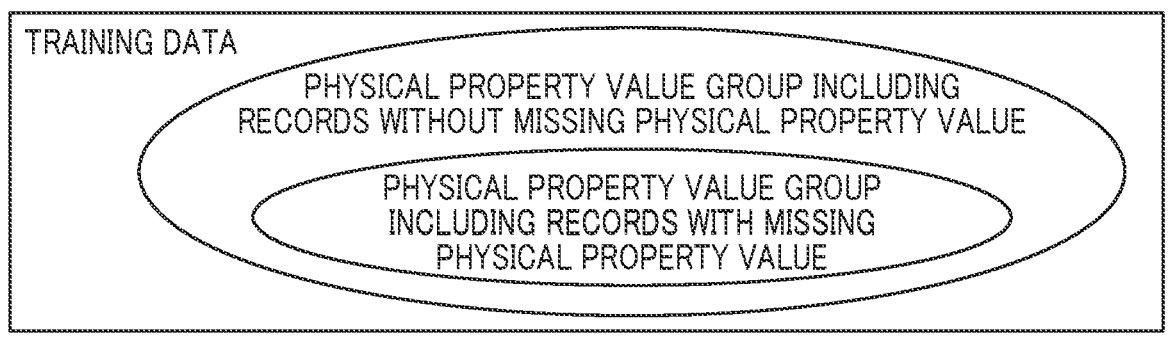
FIG. 27 schematically illustrates conditions to be satisfied by physical property values (types thereof) included in a record in the experiment data.
FIG. 28 schematically illustrates an example of structure-property relationship model training data including two types of the experiment data.

FIG. 27 schematically illustrates conditions to be satisfied by physical property values (types thereof) included in records in the experiment data. As illustrated in FIG. 27, the combination of the physical property value types in the records is required to satisfy the inclusion relation. Specifically, the record including a larger number of the physical property values (types thereof) includes all the physical property values (types thereof) of the record including a smaller number of the physical property values (types thereof). For example, it is assumed that there are three types of experiment data items.

It is assumed that the first experiment data item includes an experiment result with one type of the physical property value, the second experiment data item includes an experiment result with two types of the physical property values, and the third experiment data item includes an experiment result with three types of the physical property values. The three physical property value types in the third experiment data item include the physical property value type in the first experiment data item and the two physical property value types in the second experiment data item. The physical property value types in the second experiment data item include the physical property value type in the first experiment data and another physical property value type.

A set of physical property values in the first experiment data item (a set of physical property value columns or a set of physical property value types) is included in a set of physical property values in each of the second and third experiment data items, and the set of physical property values in the second experiment data item is included in the set of physical property values in the third experiment data item. From the first experiment data item, data on the two types of physical property values is missing and, from the second experiment data item, data on the one type of physical property values is missing. Structure-property relationship model training data is pre-processed from the experiment data so as to satisfy an inclusion relation as described above.

FIG. 28 schematically illustrates an example of the training data for the structure-property relationship model including two types of experiment data items. A first experiment data item 311 has only measurement values of a physical property value 1 (Prop1). A second experiment data item 312 has measurement values of the physical property value 1 (Prop1) and measurement values of a physical property value 2 (Prop2). In other words, a set of physical property values in the first experiment data item is included in a set of physical property values in the second experiment data item.

Figures 29, 30:
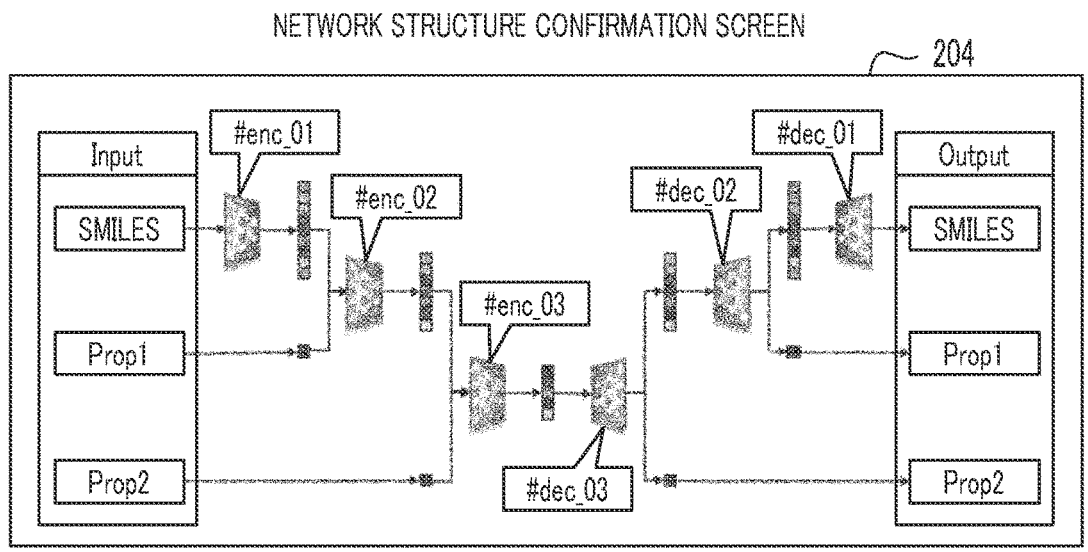
FIG. 29 illustrates an example of a network structure confirmation screen displayed by the display unit for the user in the display device according to the fourth embodiment.
FIG. 30 illustrates an example of the configuration of the model table included in the model data DB according to the third embodiment.

FIG. 29 illustrates an example of a network structure confirmation screen 204 to be displayed by the display unit P11 for the user in the display device M05 according to the fourth embodiment. FIG. 30 illustrates an example of a configuration of a model table 174 included in the model data DB17 according to the third embodiment. The model table 174 in FIG. 30 corresponds to a configuration diagram of the chemical structure formula generation model illustrated in FIG. 29.

A network structure illustrated in FIG. 29 is the same as the network structure illustrated in FIG. 21 in the second embodiment. The physical property value MWt is replaced with the physical property value Prop1, and the physical property value logP is replaced with the physical property value Prop2. Information in columns T14C1 to T14C3 in a model table 174 in FIG. 30 is the same as the information in the columns T10C1 to T10C3 in the model table 172 illustrated in FIG. 23 in the second embodiment. A Target column T14C4 indicates a table name and physical property value names (Prop1 and Prop2) in the present embodiment.

FIG. 31 illustrates an example in which the training data generation unit P02 generates, from the experiment data, the structure-property relationship model training data. An initial table 150 is generated from the experiment data, and stores the structure-property relationship model training data that has been pre-processed such that the set of physical property values satisfies the inclusion relation. The training data generation unit P02 generates, from the initial table 150, training data for each of the VAEs. Columns T15C1 to T15C4 and T15C7 in the initial table 150 indicate the same types of information as those indicated by the columns having the same names in the training table 154 illustrated in FIG. 22 in the second embodiment. Columns T15C5 and T15C6 indicate respective measurement values of Prop1 and Prop2.

The initial table 150 includes records including different sets of physical property values. Each of the records in which Table ID is "Tb1_Exp_011" includes measurement values of Prop1 and Prop1. Each of the records in which Table ID is "Tb1_Exp_012" includes only a measurement value of Prop1. The records in which Table ID is "Tb1_Exp_013" include the record including measurement values of Prop1 and Prop1 and the record including only a measurement value of Prop1.

The training data generation unit P02 extracts, from the experiment data, the records each including Prop1 and Prop2 and the records each including only Prop1, and stores Null in a Prop2 field of each of the records including only Prop1. The training data generation unit P02 stores these records in the initial table 150, and sorts the records according to the number of Nulls (e.g., in ascending order).

Then, the training data generation unit P02 generates, from the initial table 150, a training table 157 for the first VAE in the structure-property relationship model and a training table 158 for the second VAE in the structure-property relationship model.

The training table 157 for the first VAE in the structure-property relationship model is the training data for the outer VAE (#enc_02 and #dec_2) of the structure-property relationship model. The first VAE training table 157 includes the records including the measurement values of Prop1 in the initial table 150, i.e., all the records. Columns T16C1 to T16C5 and T16C7 indicate the same types of information as that indicated by the columns having the same names in the initial table. From the first VAE training table 157, the Prop2 column in the initial table 150 has been deleted. The physical property value required to train the first VAE (#enc_02 and #dec_02) is only Prop1 included in the input to the first VAE and in the output thereof.

The training table 158 for the second VAE in the structure-property relationship model is training data for the inner VAE (#enc_03 and #dec_3) of the structure-property relationship model. The second VAE training table 158 includes the records each including the measurement values of Prop1 and Prop2 in the initial table 150. Columns T17C1 to T17C7 indicate the same types of information items as that indicated by the columns having the same names in the initial table.

To train the second VAE, it is necessary to rebuild and connect the outer two encoders #enc_01 and #enc_02 to each other. Accordingly, the training data includes, in addition to Prop2 corresponding to the input/output physical property values of the second VAE, Prop1 corresponding to the input physical property value of the encoder #enc_02.

As described in the second to fourth embodiments, the training data for the structure-property relationship model includes the plurality of (group of) training tables to be used to train the plurality of individual VAEs. Each of the training tables associates each of the compound structure representations with measurement values of one or more predetermined physical property value types. Of any two of the training tables, the training table having a larger number of the physical property value types includes all the physical property value types and all the compound structure representations in the training table having a smaller number of the physical property value types. The training table having the larger number of physical property value types is used to train the inner VAEs in the structure-property relationship model.

As described in the present fourth embodiment, the training data is configured, from the experiment data including the records with the missing physical property values, to include the records having the inclusion relation between the sets of physical property values described above. This allows the training data for each of the VAEs in the structure-property relationship model to be configured to include the records including, in addition to the input/output physical property values of the VAEs, all the physical property values input to the outer encoder. As a result, it is possible to appropriately train each of the VAEs.

Note that the present invention is not limited to the embodiments described above, and includes various modifications. For example, the embodiments described above have been described in detail for the purpose of clear description of the present invention, and the present invention is not necessarily limited to those including all the described configurations. A part of a configuration of one of the embodiments can be substituted with a configuration of another of the embodiments and, to the configuration of the one embodiment, the configuration of the other embodiment can also be added. A part of a configuration of each of the embodiments may be added to another configuration, deleted, or replaced with another configuration.

A part or all of the above-described configurations, functions, processing units, and the like may be implemented as hardware by being designed using, e.g., an integrated circuit. Alternatively, each of the above-described configurations, functions, and the like may be implemented as software by allowing a processor to interpret and execute a program for implementing each of the functions. Information such as the program for implementing each of the functions, tables, and files can be placed in a recording device such as a memory, hard disk, or SSD (Solid State Drive) or a recording medium such as an IC card or SD card.

The drawings show control lines and information lines considered to be necessary for explanation, and do not show all control lines or information lines in the products. It may also be considered that substantially all configurations are actually interconnected.

The invention claimed is:

1. A system for generating a compound structure representation, the system comprising:
   one or more processors; and
   one or more storage devices,
   wherein each of the one or more storage devices stores a structure model, a structure-property relationship model, a compound structure representation of each of one or more known materials, and one or more target values of each of one or more types of physical property values,
wherein the structure model includes:
a first encoder that converts the compound structure representation to a real number vector; and
a first decoder that estimates the compound structure representation from the real number vector resulting from the conversion by the first encoder,
wherein the structure-property relationship model includes:
a second encoder that converts, to a real number vector, an input vector including, as components, the real number vector generated by the first encoder and a target value vector including the target values of the one or more types of physical property values; and
a second decoder that estimates the input vector from the real number vector generated by the second encoder,
wherein each of the one or more processors generates, using the first encoder of the structure model, one or more structure generation vectors on the basis of each of the compound structure representation of each of the one or more known materials and the one or more target values of each of the one or more types of physical property values,
wherein each of the one or more structure generation vectors includes, as components, the real number vector of the compound structure representation of one of the known materials generated by the first encoder and the target value vector including the target values of each of the one or more types of physical property values,
wherein each of the one or more processors inputs, to the structure-property relationship model, each of the one or more structure generation vectors, extracts, from an output of the second decoder of the structure-property relationship model, the real number vector corresponding to the compound structure representation, and inputs the extracted real number vector to the first decoder of the structure model and generates a novel compound structure representation,
wherein each of the one or more storage devices includes, in addition to the one or more target values of each of the one or more types of physical property values, one or more target values of each of one or more other types of physical property values,
wherein the structure-property relationship model includes a plurality of auto-encoders,
wherein the first auto-encoder included in the plurality of auto-encoders includes the second encoder and the second decoder,
wherein each of encoders included in the plurality of auto-encoders and other then the first auto-encoder is interposed between the encoder and a decoder of another of the auto-encoders,
wherein an input to each of the auto-encoders other than the first auto-encoder includes, as components, a real number vector from the decoder of the other auto-encoder and the target value vector including the target values of each of the one or more types of physical property values selected from among the one or more other types of physical property values,
wherein each of the one or more storage devices stores training data for the structure-property relationship model,
wherein each of the one or more processors trains the structure-property relationship model by using the training data,
wherein the training data includes a plurality of groups to be used to train the plurality of respective auto-encoders,
wherein each of the plurality of groups associates each of a plurality of compound structure representations with measurement values of one or more predetermined types of physical property values,
wherein, of two groups included in the plurality of groups, one group having a larger number of types of physical property values includes all the types of physical property values and all the compound structure representations of another group having a smaller number of types of physical property values, and
wherein the group having the larger number of types of the physical property values is used to train the inner auto-encoder in the structure-property relationship model.

2. The system according to claim 1,
wherein each of the one or more storage devices stores a first compound structure representation group associated with measurement values of the one or more types of physical property values, and
wherein each of the one or more processors trains the structure model by using the first compound structure representation group, and trains the structure-property relationship model by using the measurement values of the one or more types of physical property values and a result of conversion of the first compound structure representation group by the structure model.

3. The system according to claim 1,
wherein each of the one or more storage devices stores a first compound structure representation group associated with measurement values of the one or more types of physical property values and a second compound structure representation group unassociated with the measurement values of the one or more types of physical property values, and
wherein each of the one or more processors trains the structure model by using the first compound structure representation group and the second compound structure representation group, and trains the structure-property relationship model by using the measurement values of the one or more types of physical property values and a result of conversion of the first compound structure representation group by the first encoder.

4. The system according to claim 1,
wherein the types of the physical property values of the target values input to the plurality of auto-encoders are different from each other, and
wherein the number of the target values input to each of the plurality of auto-encoders is 1.

5. The system according to claim 1,
wherein the types of the physical property values of the target values input to the plurality of auto-encoders are different from each other, and
wherein the plurality of auto-encoders include the auto-encoders to which different numbers of the target values are input.

6. The system according to claim 1,
wherein, in the plurality of auto-encoders, an amount of training data for the outer auto-encoder is larger than an amount of training data for the inner auto-encoder.

7. The system according to claim 1,
wherein each of the one or more processors displays a network structure including the structure model and the structure-property relationship model, and corrects the network structure according to a user input to the network structure.

8. A method of causing a system to generate a compound structure representation, the system including:
one or more processors; and
one or more storage devices,
wherein each of the one or more storage devices stores a structure model, a structure-property relationship model, a compound structure representation of each of one or more known materials, and one or more target values of each of one or more types of physical property values,
wherein the structure model includes:
a first encoder that converts the compound structure representation to a real number vector; and
a first decoder that estimates the compound structure representation from the real number vector resulting from the conversion by the first encoder,
wherein the structure-property relationship model includes:
a second encoder that converts, to a real number vector, an input vector including, as components, the real number vector generated by the first encoder and a target value vector including the target values of the one or more types of physical property values; and
a second decoder that estimates the input vector from the real number vector generated by the second encoder,
the method comprising:
each of the one or more processors generating, using the first encoder of the structure model, one or more structure generation vectors on the basis of each of the compound structure representation of each of the one or more known materials and the one or more target values of each of the one or more types of physical property values,
wherein each of the one or more structure generation vectors includes, as components, the real number vector of the compound structure representation of one of the known materials generated by the first encoder and the target value vector including the target values of each of the one or more types of physical property values,
the method further comprising:
each of the one or more processors inputting, to the structure-property relationship model, each of the one or more structure generation vectors, extracting, from an output of the second decoder of the structure-property relationship model, the real number vector corresponding to the compound structure representation, and inputting the extracted real number vector to the first decoder of the structure model and generating a novel compound structure representation,
wherein each of the one or more storage devices includes, in addition to the one or more target values of each of the one or more types of physical property values, one or more target values of each of one or more other types of physical property values,
wherein the structure-property relationship model includes a plurality of auto-encoders,
wherein the first auto-encoder included in the plurality of auto-encoders includes the second encoder and the second decoder,
wherein each of encoders included in the plurality of auto-encoders and other then the first auto-encoder is interposed between the encoder and a decoder of another of the auto-encoders,
wherein an input to each of the auto-encoders other than the first auto-encoder includes, as components, a real number vector from the decoder of the other auto-encoder and the target value vector including the target values of each of the one or more types of physical property values selected from among the one or more other types of physical property values
wherein each of the one or more storage devices stores training data for the structure-property relationship model,
wherein each of the one or more processors trains the structure-property relationship model by using the training data,
wherein the training data includes a plurality of groups to be used to train the plurality of respective auto-encoders,
wherein each of the plurality of groups associates each of a plurality of compound structure representations with measurement values of one or more predetermined types of physical property values,
wherein, of two groups included in the plurality of groups, one group having a larger number of types of physical property values includes all the types of physical property values, and all the compound structure representations of another group having a smaller number of types of physical property values, and
wherein the group having the larger number of types of the physical property values is used to train the inner auto-encoder in the structure-property relationship model.

* * * * *